(12) United States Patent
Garcia et al.

(10) Patent No.: US 11,142,577 B2
(45) Date of Patent: Oct. 12, 2021

(54) WNT SIGNALING AGONIST MOLECULES

(71) Applicants: The Board of Trustees of the Leland Stanford Junior University, Stanford, CA (US); University of Washington, Seattle, WA (US)

(72) Inventors: Kenan Christopher Garcia, Menlo Park, CA (US); David Baker, Seattle, WA (US); Claudia Yvonne Janda, Palo Alto, CA (US); Luke Dang, Carnation, WA (US); James Daniel Moody, Bozeman, MT (US)

(73) Assignees: The Board of Trustees of the Leland Stanford Junior University, Stanford, CA (US); University of Washington, Seattle, WA (US)

( * ) Notice: Subject to any disclaimer, the term of this patent is extended or adjusted under 35 U.S.C. 154(b) by 729 days.

(21) Appl. No.: 15/508,779

(22) PCT Filed: Sep. 11, 2015

(86) PCT No.: PCT/US2015/049829
§ 371 (c)(1),
(2) Date: Mar. 3, 2017

(87) PCT Pub. No.: WO2016/040895
PCT Pub. Date: Mar. 17, 2016

(65) Prior Publication Data
US 2017/0306029 A1 Oct. 26, 2017

Related U.S. Application Data

(60) Provisional application No. 62/206,150, filed on Aug. 17, 2015, provisional application No. 62/049,949, filed on Sep. 12, 2014, provisional application No. 62/345,594, filed on Jun. 3, 2016.

(51) Int. Cl.
*C07K 16/28* (2006.01)
*C07K 16/30* (2006.01)

(52) U.S. Cl.
CPC .......... *C07K 16/2863* (2013.01); *C07K 16/28* (2013.01); *C07K 16/30* (2013.01); *C07K 2317/21* (2013.01); *C07K 2317/31* (2013.01); *C07K 2317/565* (2013.01); *C07K 2317/569* (2013.01); *C07K 2317/622* (2013.01); *C07K 2317/75* (2013.01); *C07K 2317/92* (2013.01); *C07K 2318/20* (2013.01); *C07K 2319/00* (2013.01)

(58) Field of Classification Search
None
See application file for complete search history.

(56) References Cited

U.S. PATENT DOCUMENTS

| | | |
|---|---|---|
| 6,005,079 A | 12/1999 | Casterman et al. |
| 7,982,013 B2 | 7/2011 | Gurney et al. |
| 8,202,966 B2 | 6/2012 | McCarthy |
| 8,221,751 B2 | 7/2012 | Nakamura et al. |
| 8,343,922 B2 | 1/2013 | Wu et al. |
| 8,461,155 B2 | 6/2013 | Wu et al. |
| 8,507,442 B2 | 8/2013 | Gurney et al. |
| 8,637,506 B2 | 1/2014 | Wu et al. |
| 8,715,941 B2 | 5/2014 | Abo et al. |
| 8,846,041 B2 | 9/2014 | Bourhis et al. |
| 8,859,736 B2 | 10/2014 | Ma et al. |
| 8,883,735 B2 | 11/2014 | Jenkins et al. |
| 8,975,044 B2 | 3/2015 | Gurney et al. |
| 9,359,444 B2 | 6/2016 | Dupont et al. |
| 2005/0261181 A1 | 11/2005 | Wu et al. |
| 2006/0127393 A1 | 6/2006 | Li et al. |
| 2007/0196872 A1 | 8/2007 | Bex et al. |
| 2008/0286261 A1 | 11/2008 | Morgan et al. |
| 2009/0311243 A1 | 12/2009 | Brockbank et al. |
| 2010/0129375 A1* | 5/2010 | Junge ................ A61K 39/3955 514/1.1 |
| 2010/0254980 A1 | 10/2010 | Cong et al. |
| 2011/0105606 A1 | 5/2011 | Rabbani et al. |
| 2012/0322717 A9 | 12/2012 | Liu et al. |
| 2013/0058934 A1 | 3/2013 | Cong et al. |
| 2013/0064823 A1 | 3/2013 | Cong et al. |
| 2013/0095097 A1 | 4/2013 | Blankenship et al. |
| 2013/0183320 A1 | 7/2013 | Wu et al. |
| 2013/0230521 A1 | 9/2013 | Nakamura et al. |
| 2013/0253172 A1 | 9/2013 | Gurney et al. |
| 2014/0044713 A1 | 2/2014 | De Lau et al. |

(Continued)

FOREIGN PATENT DOCUMENTS

| | | |
|---|---|---|
| EP | 2910550 A2 | 8/2015 |
| EP | 3191526 | 9/2015 |

(Continued)

OTHER PUBLICATIONS

Bourhis et al (Journal of Biological Chemistry, 2010, 285:9172-9179).*

(Continued)

*Primary Examiner* — Laura B Goddard
(74) *Attorney, Agent, or Firm* — Pamela J. Sherwood; Bozicevic, Field & Francis LLP

(57) ABSTRACT

Wnt signaling agonist compositions and methods for their use are provided. Wnt signaling agonists of the invention comprise a frizzled binding moiety, which is fused or conjugated to an LRP5 or LRP6 binding moiety.

5 Claims, 16 Drawing Sheets
(7 of 16 Drawing Sheet(s) Filed in Color)
Specification includes a Sequence Listing.

(56) References Cited

U.S. PATENT DOCUMENTS

| | | |
|---|---|---|
| 2014/0154252 A1 | 6/2014 | Thompson et al. |
| 2014/0200179 A1 | 7/2014 | Garcia et al. |
| 2014/0242078 A1 | 8/2014 | Dupont et al. |
| 2014/0363439 A1 | 12/2014 | Bourhis et al. |
| 2015/0119555 A1 | 4/2015 | Jung et al. |
| 2015/0209407 A1 | 7/2015 | Pignolo |
| 2015/0376252 A1* | 12/2015 | Xu .................. A61K 35/74 514/7.6 |
| 2016/0152947 A1 | 6/2016 | Pioszak |
| 2016/0312207 A1 | 10/2016 | Kuo et al. |
| 2017/0306029 A1 | 10/2017 | Garcia et al. |

FOREIGN PATENT DOCUMENTS

| | | |
|---|---|---|
| JP | 2012516685 | 7/2012 |
| WO | 2007/146968 A2 | 12/2007 |
| WO | 2008/134632 A1 | 11/2008 |
| WO | 2010/016766 A2 | 2/2010 |
| WO | 2010090513 | 8/2010 |
| WO | 2011/090762 A1 | 7/2011 |
| WO | 2012103360 | 8/2012 |
| WO | 2012/140274 A2 | 10/2012 |
| WO | 2013/092001 A1 | 6/2013 |
| WO | 2014/029752 A1 | 2/2014 |
| WO | 2014/124326 A1 | 8/2014 |
| WO | 2014/159580 A1 | 10/2014 |
| WO | 2015/036582 A2 | 3/2015 |
| WO | 2015063187 | 5/2015 |
| WO | 2015063187 A1 | 5/2015 |
| WO | 2016040895 | 3/2016 |

OTHER PUBLICATIONS

Chen et al (Cellular Signalling, 2014, 26:1068-1074).*
Sebastian et al (PLoS One, Nov. 27, 2017, 12(11):e0188264, internet pp. 1-19).*
Dijksterhuis et al (Journal of Biological Chemistry, 2015, 290:6789-6798).*
Ke et al (Genes & Development, 2013, 27:2305-2319, in IDS).*
Zhang et al (Scientific Reports, 2014, 5:09803, internet pp. 1-13).*
Getz et al., "Protease-resistant peptide ligands from a knottin scaffold library", ACS Chem Bioi., Aug. 19, 2011, pp. 837-844, vol. 6. No. 8, ACS Publications, Washington, DC.
Ke et al., "Structure and function of Norrin in assembly and activation of a Frizzled 4-Lrp5/6 complex", Genes Dev., 2013, pp. 2305-2319, vol. 27. No. 21, Cold Spring Harbor Laboratory, Huntington, NY.
Holmen et al., "Wnt-independent activation of β-catenin mediated by a Dkk1-Fz5 fusion protein", Biochem Biophys Res Commun., Mar. 11, 2005, p. 533-539, 328(2), Elsevier, Amsterdam, Netherlands.
Mikels et al., "Wnts as ligands: processing, secretion and reception", Oncogene, 2006, pp. 7461-7468, 25, Nature Publishing Group, London, United Kingdom.
Bourhis et al. (2010) "Reconstitution of a frizzled8-Wnt3a-LRP6 signaling complex reveals multiple Wnt and Dkk1 binding sites on LRP6" 285;12 Pgs: 9172-9179.
Chen et al. (2014) "Disseminated, persistent, and fatal infection due to the vaccine strain of varicella-zoster virus in an adult following stem cell transplantation", 60;7 pgs: 1068-1074.
Dijksterhuis et al. (2015) Systematic Mapping of WNT-FZD Protein Interactions Reveals Functional Selectivity by Distinct WNT-FZD Pairs.
Phillipe et al. (2010) WNT Modulators in the Biotech Pipeline Developmental Dynamics 239:102-114.
Clevers et al.(2012) "Wnt/b-Catenin Signaling and Disease" Cell: 149:1192-1205.
Janda et al. (2012) "Structural basis of Wnt recognition by Frizzled" Science; 337:59-64.
Chang et al. "Structure and functional properties of Norrin mimic Wnt for signalling with Frizzled4, Lrp5/6, and proteoglycane" Life. 2015:4 1-27.
Gurney et al. (2012) "Wnt pathway inhibition via the targeting of Frizzled receptors results in decreased growth and tumorigenicity of human tumors", PNAS, 11717-11722.
Minear et al. "Wnt proteins promote bone regeneration.", Science Translational Medicine Apr. 28, 2010, vol. 2, No. 29, Apr. 28, 2010 (Apr. 28, 2010), p. 29ra30.
Liu et al. "A small-molecule agonist of the Wnt signaling pathway", Angewandte Chemie International Edition, Verlag Chemie, vol. 44, No. 13, Mar. 18, 2005 (Mar. 18, 2005), pp. 1987-1990.
Janda et al. "Surrogate Wnt agonists that phenocopy canonical Wnt and [beta]-catenin signalling", Nature,vol. 545, No. 7653, May 3, 2017 (May 3, 2017), pp. 234-237.
Kahn et al. "Can we safely target the WNT pathway?", Nature Reviews. Drug Discovery, vol. 13, No. 7, Jul. 1, 2014 (Jul. 1, 2014), pp. 513-532.
Jean-Philippe et al "Wnt Modulators in the Biotech Pipeline", Developmental Dynamics, Wiley-Liss, Inc., New York, NY, US, val. 239, No. 1, Jan. 1, 2010 (Jan. 1, 2010), pp. 102-114.
Rey et al. (2010) "Wnt modulators in biotech pipeline" Developmental Dynamics 239:1 102-114.
Blagodatski et al (2014) "Targeting the Wnt pathways for therapies", Molecular and Cellular Therapies, 2:28, pp. 1-15.

* cited by examiner

Signal peptide | OMP-18R5 light chain variable region

MLLVNQSHQGFNKEHTSMVSAIVLYVLLAAAAHSAFAADPIELTQPPSVSVAPGQTARISCSGDNIGSFYVHWYQQKPGQAPVLV

IYDKSNRPSGIPERFSGSNSGNTATLTISGTQAEDEADYYCQSYANTLSLVFGGGTKLTVLGTTAASGSSGGSGAEVQLVESGG

| OMP-18R5 heavy chain variable region | Linker peptide

GLVQPGGSLRL

The Wnt surrogate agonist scFv(Onco)-DKK1c enhance the accumulation of cytoplasmic beta-catenin in SY5Y cells:

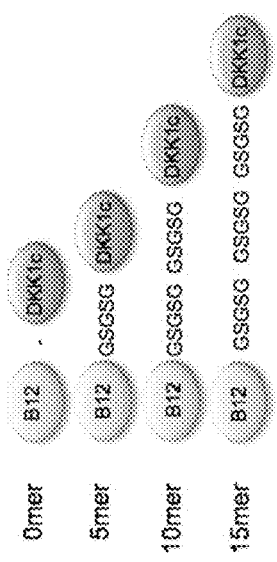
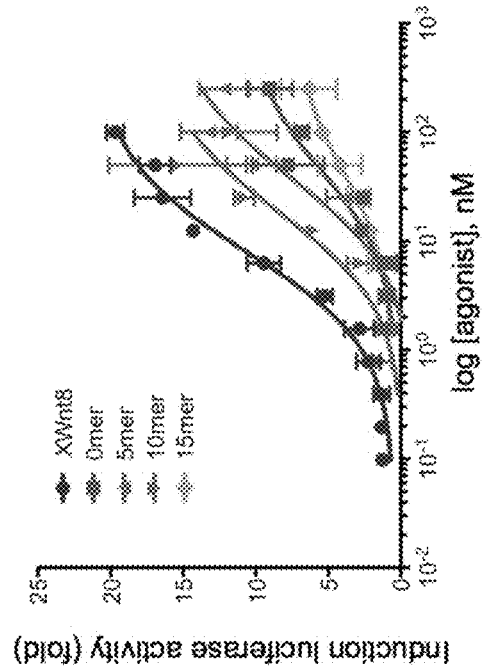
FIG. 13A
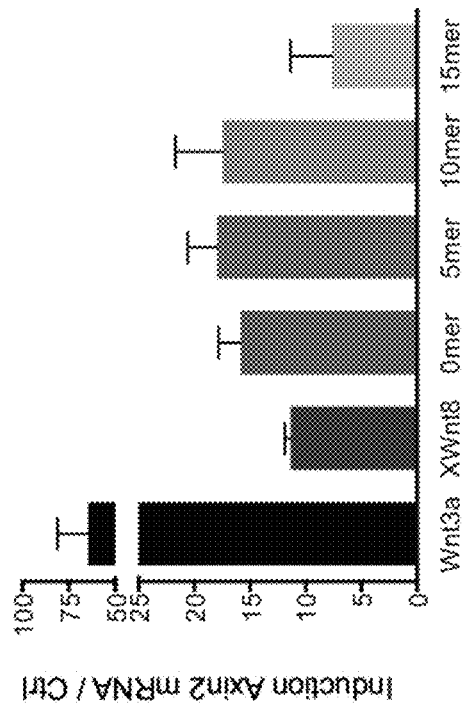
FIG. 13B

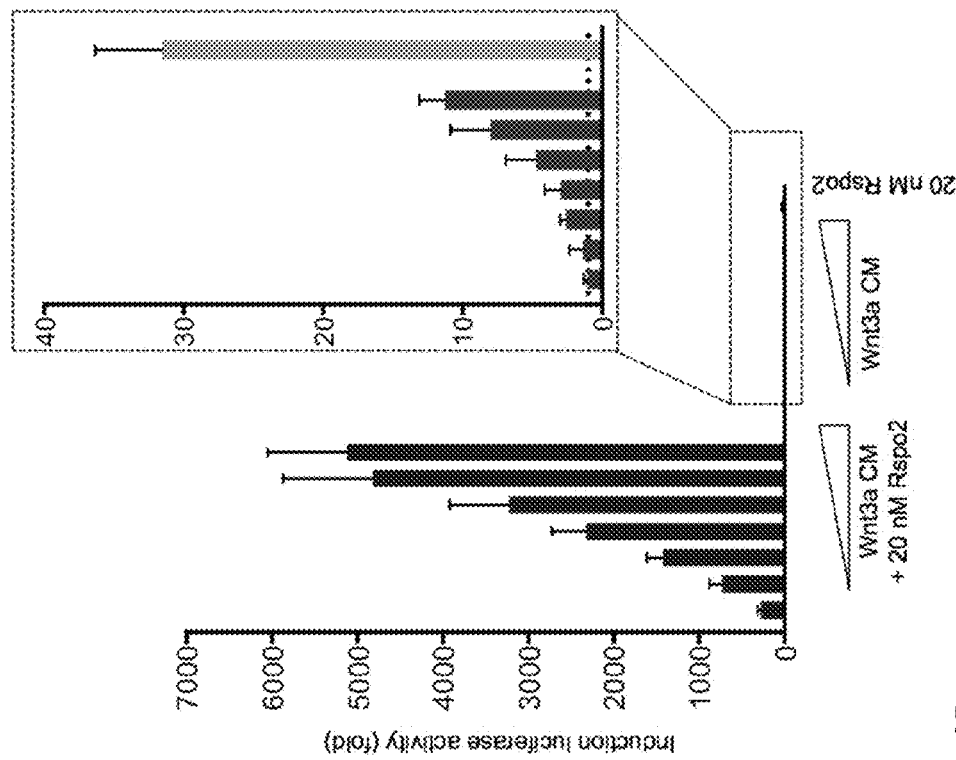
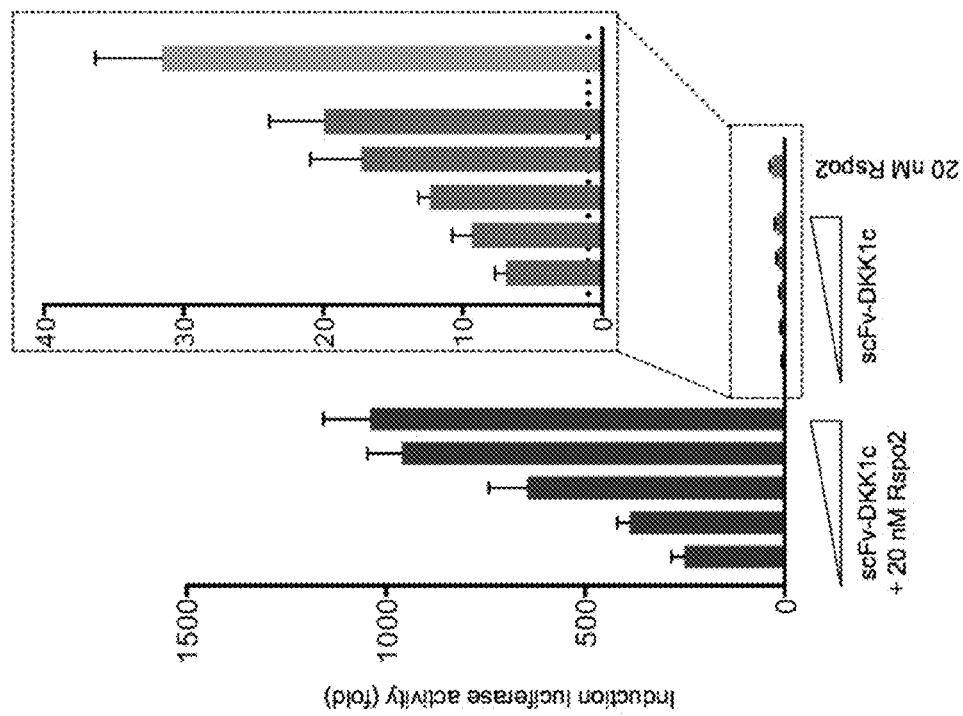
FIG. 15

SEQUENCE LISTING

<160> NUMBER OF SEQ ID NOS: 39

<210> SEQ ID NO 1
<211> LENGTH: 10
<212> TYPE: PRT
<213> ORGANISM: Artificial sequence
<220> FEATURE:
<223> OTHER INFORMATION: synthetic amino acid sequence
<400> SEQUENCE: 1

Gly Phe Thr Phe Ser His Tyr Thr Leu Ser
1               5                   10

<210> SEQ ID NO 2
<211> LENGTH: 17
<212> TYPE: PRT
<213> ORGANISM: Artificial sequence
<220> FEATURE:
<223> OTHER INFORMATION: synthetic amino acid sequence
<400> SEQUENCE: 2

Val Ile Ser Gly Asp Gly Ser Tyr Thr Tyr Tyr Ala Asp Ser Val Lys
1               5                   10                  15

Gly

<210> SEQ ID NO 3
<211> LENGTH: 9
<212> TYPE: PRT
<213> ORGANISM: Artificial sequence
<220> FEATURE:
<223> OTHER INFORMATION: synthetic amino acid sequence
<400> SEQUENCE: 3

Asn Phe Ile Lys Tyr Val Phe Ala Asn
1               5

<210> SEQ ID NO 4
<211> LENGTH: 11
<212> TYPE: PRT
<213> ORGANISM: Artificial sequence
<220> FEATURE:
<223> OTHER INFORMATION: synthetic amino acid sequence
<400> SEQUENCE: 4

Ser Gly Asp Lys Leu Gly Lys Lys Tyr Ala Ser
1               5                   10

<210> SEQ ID NO 5
<211> LENGTH: 8
<212> TYPE: PRT
<213> ORGANISM: Artificial sequence
<220> FEATURE:
<223> OTHER INFORMATION: synthetic amino acid sequence
<400> SEQUENCE: 5

Glu Lys Asp Asn Arg Pro Ser Gly
1               5

<210> SEQ ID NO 6
<211> LENGTH: 9
<212> TYPE: PRT
<213> ORGANISM: Artificial sequence
<220> FEATURE:
<223> OTHER INFORMATION: synthetic amino acid sequence
<400> SEQUENCE: 6

-continued

```
Ser Ser Phe Ala Gly Asn Ser Leu Glu
1               5
```

<210> SEQ ID NO 7
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 7

```
Ser Gly Asp Asn Ile Gly Ser Phe Tyr Val His
1               5                   10
```

<210> SEQ ID NO 8
<211> LENGTH: 8
<212> TYPE: PRT
<213> ORGANISM: Artificial sequence
<220> FEATURE:
<223> OTHER INFORMATION: synthetic amino acid sequence

<400> SEQUENCE: 8

```
Asp Lys Ser Asn Arg Pro Ser Gly
1               5
```

<210> SEQ ID NO 9
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 9

```
Gln Ser Tyr Ala Asn Thr Leu Ser Leu
1               5
```

<210> SEQ ID NO 10
<211> LENGTH: 381
<212> TYPE: PRT
<213> ORGANISM: Artificial sequence
<220> FEATURE:
<223> OTHER INFORMATION: synthetic amino acid sequence

<400> SEQUENCE: 10

```
Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro Ile Glu Leu Thr Gln Pro Pro
        35                  40                  45

Ser Val Ser Val Ala Pro Gly Gln Thr Ala Arg Ile Ser Cys Ser Gly
    50                  55                  60

Asp Asn Ile Gly Ser Phe Tyr Val His Trp Tyr Gln Gln Lys Pro Gly
65                  70                  75                  80

Gln Ala Pro Val Leu Val Ile Tyr Asp Lys Ser Asn Arg Pro Ser Gly
                85                  90                  95

Ile Pro Glu Arg Phe Ser Gly Ser Asn Ser Gly Asn Thr Ala Thr Leu
            100                 105                 110

Thr Ile Ser Gly Thr Gln Ala Glu Asp Glu Ala Asp Tyr Tyr Cys Gln
        115                 120                 125

Ser Tyr Ala Asn Thr Leu Ser Leu Val Phe Gly Gly Gly Thr Lys Leu
    130                 135                 140
```

```
Thr Val Leu Gly Thr Thr Ala Ala Ser Gly Ser Ser Gly Gly Ser Ser
145                 150                 155                 160

Ser Gly Ala Glu Val Gln Leu Val Glu Ser Gly Gly Gly Leu Val Gln
            165                 170                 175

Pro Gly Gly Ser Leu Arg Leu Ser Cys Ala Ala Ser Gly Phe Thr Phe
            180                 185                 190

Ser His Tyr Thr Leu Ser Trp Val Arg Gln Ala Pro Gly Lys Gly Leu
            195                 200                 205

Glu Trp Val Ser Val Ile Ser Gly Asp Gly Ser Tyr Thr Tyr Tyr Ala
210                 215                 220

Asp Ser Val Lys Gly Arg Phe Thr Ile Ser Ser Asp Asn Ser Lys Asn
225                 230                 235                 240

Thr Leu Tyr Leu Gln Met Asn Ser Leu Arg Ala Glu Asp Thr Ala Val
            245                 250                 255

Tyr Tyr Cys Ala Arg Asn Phe Ile Lys Tyr Val Phe Ala Asn Trp Gly
            260                 265                 270

Gln Gly Thr Leu Val Thr Val Ser Gly Ser Gly Ser Lys Met Tyr
            275                 280                 285

His Thr Lys Gly Gln Glu Gly Ser Val Cys Leu Arg Ser Ser Asp Cys
290                 295                 300

Ala Ser Gly Leu Cys Cys Ala Arg His Phe Trp Ser Lys Ile Cys Lys
305                 310                 315                 320

Pro Val Leu Lys Glu Gly Gln Val Cys Thr Lys His Arg Arg Lys Gly
            325                 330                 335

Ser His Gly Leu Glu Ile Phe Gln Arg Cys Tyr Cys Gly Glu Gly Leu
            340                 345                 350

Ser Cys Arg Ile Gln Lys Asp His His Gln Ala Ser Asn Ser Ser Arg
            355                 360                 365

Leu His Thr Cys Gln Arg His His His His His His
            370                 375                 380

<210> SEQ ID NO 11
<211> LENGTH: 6
<212> TYPE: PRT
<213> ORGANISM: Artificial sequence
<220> FEATURE:
<223> OTHER INFORMATION: synthetic amino acid sequence

<400> SEQUENCE: 11

Leu Leu Glu Arg Ile Tyr
1               5

<210> SEQ ID NO 12
<211> LENGTH: 6
<212> TYPE: PRT
<213> ORGANISM: Artificial sequence
<220> FEATURE:
<223> OTHER INFORMATION: synthetic amino acid sequence

<400> SEQUENCE: 12

Thr Leu Glu Arg Val Tyr
1               5

<210> SEQ ID NO 13
<211> LENGTH: 6
<212> TYPE: PRT
<213> ORGANISM: Artificial sequence
<220> FEATURE:
<223> OTHER INFORMATION: synthetic amino acid sequence
```

```
<400> SEQUENCE: 13

Leu Leu Ile Asn Ile Tyr
1               5

<210> SEQ ID NO 14
<211> LENGTH: 15
<212> TYPE: PRT
<213> ORGANISM: Artificial sequence
<220> FEATURE:
<223> OTHER INFORMATION: synthetic amino acid sequence

<400> SEQUENCE: 14

Lys Tyr Ala Ala Ala Val Ala Ala Phe Ala Ala Ala Ala Gly Phe
1               5                   10                  15

<210> SEQ ID NO 15
<211> LENGTH: 15
<212> TYPE: PRT
<213> ORGANISM: Artificial sequence
<220> FEATURE:
<223> OTHER INFORMATION: synthetic amino acid sequence

<400> SEQUENCE: 15

Lys Tyr Val Ala Ala Val Ala Thr Phe Ala Leu Gln Ala Gly Phe
1               5                   10                  15

<210> SEQ ID NO 16
<211> LENGTH: 15
<212> TYPE: PRT
<213> ORGANISM: Artificial sequence
<220> FEATURE:
<223> OTHER INFORMATION: synthetic amino acid sequence

<400> SEQUENCE: 16

Lys Tyr Lys Glu Leu Val Lys Glu Phe Val Gly Asp Ala Val Glu
1               5                   10                  15

<210> SEQ ID NO 17
<211> LENGTH: 123
<212> TYPE: PRT
<213> ORGANISM: Artificial sequence
<220> FEATURE:
<223> OTHER INFORMATION: synthetic amino acid sequence

<400> SEQUENCE: 17

Met Gly Val Ser Phe Ser Glu Val Met Gly Lys Gln Lys Asp Glu Gln
1               5                   10                  15

Ala Arg Glu Gln Leu Lys Glu Gly Met Lys Lys Ile Glu Glu Gln Gly
                20                  25                  30

Lys Lys Leu Ser Glu Thr Arg Thr Gln Glu Glu Leu Gln Lys Tyr Ala
            35                  40                  45

Ala Ala Val Ala Ala Phe Ala Ala Ala Gly Phe Leu Gly Lys Asn
        50                  55                  60

Leu Glu Glu Arg Arg Gly Phe Asn Arg Gly Lys Leu Glu Ile Gly
65                  70                  75                  80

Lys Ile Ser Gly Glu Val Tyr Lys Leu Leu Asp Leu Lys Ala
                85                  90                  95

Val Arg Ala Lys Glu Lys Lys Gly Leu Asp Ile Leu Asn Met Val Gly
                100                 105                 110

Glu Ile Lys Gly Leu Leu Glu Arg Ile Tyr Ala
            115                 120
```

<210> SEQ ID NO 18
<211> LENGTH: 123
<212> TYPE: PRT
<213> ORGANISM: Artificial sequence
<220> FEATURE:
<223> OTHER INFORMATION: synthetic amino acid sequence

<400> SEQUENCE: 18

```
Met Gly Val Ser Phe Ser Glu Val Met Gly Lys Gln Lys Asp Glu Gln
1               5                   10                  15

Ala Arg Glu Gln Leu Lys Glu Gly Met Ile Lys Ile Glu Glu Gln Gly
                20                  25                  30

Lys Lys Leu Ser Glu Thr Arg Thr Gln Glu Glu Leu Gln Lys Tyr Val
            35                  40                  45

Ala Ala Val Ala Thr Phe Ala Leu Gln Ala Gly Phe Leu Gly Pro Asn
        50                  55                  60

Leu Glu Glu Arg Arg Gly Phe Asn Arg Arg Gly Lys Glu Glu Ile Gly
65                  70                  75                  80

Lys Ile Ser Gly Glu Val Tyr Leu Lys Leu Leu Asp Leu Lys Lys Ala
                85                  90                  95

Val Arg Ala Lys Glu Lys Lys Gly Leu Asp Ile Leu Asn Met Val Gly
                100                 105                 110

Glu Ile Lys Gly Thr Leu Glu Arg Val Tyr Ala
            115                 120
```

<210> SEQ ID NO 19
<211> LENGTH: 6
<212> TYPE: PRT
<213> ORGANISM: Artificial sequence
<220> FEATURE:
<223> OTHER INFORMATION: synthetic amino acid sequence

<400> SEQUENCE: 19

```
Gly Ser Gly Ser Gly Ser
1               5
```

<210> SEQ ID NO 20
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 20

```
Gly Ser Gly Ser Gly
1               5
```

<210> SEQ ID NO 21
<211> LENGTH: 10
<212> TYPE: PRT
<213> ORGANISM: Artificial sequence
<220> FEATURE:
<223> OTHER INFORMATION: synthetic amino acid sequence

<400> SEQUENCE: 21

```
Gly Ser Gly Ser Gly Gly Ser Gly Ser Gly
1               5                   10
```

<210> SEQ ID NO 22
<211> LENGTH: 15
<212> TYPE: PRT
<213> ORGANISM: Artificial sequence
<220> FEATURE:
<223> OTHER INFORMATION: synthetic amino acid sequence -continued

<400> SEQUENCE: 22

```
Gly Ser Gly Ser Gly Gly Ser Gly Ser Gly Gly Ser Gly Ser Gly
1               5                   10                  15
```

<210> SEQ ID NO 23
<211> LENGTH: 7
<212> TYPE: PRT
<213> ORGANISM: Artificial sequence
<220> FEATURE:
<223> OTHER INFORMATION: synthetic amino acid sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 23

```
Pro Pro Pro Ser Pro Xaa Ser
1               5
```

<210> SEQ ID NO 24
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 24

```
Pro Pro Pro Ser Pro
1               5
```

<210> SEQ ID NO 25
<211> LENGTH: 90
<212> TYPE: PRT
<213> ORGANISM: Homo sapiens

<400> SEQUENCE: 25

```
Lys Met Tyr His Thr Lys Gly Gln Glu Gly Ser Val Cys Leu Arg Ser
1               5                   10                  15

Ser Asp Cys Ala Ser Gly Leu Cys Cys Ala Arg His Phe Trp Ser Lys
                20                  25                  30

Ile Cys Lys Pro Val Leu Lys Glu Gly Gln Val Cys Thr Lys His Arg
            35                  40                  45

Arg Lys Gly Ser His Gly Leu Glu Ile Phe Gln Arg Cys Tyr Cys Gly
        50                  55                  60

Glu Gly Leu Ser Cys Arg Ile Gln Lys Asp His His Gln Ala Ser Asn
65                  70                  75                  80

Ser Ser Arg Leu His Thr Cys Gln Arg His
                85                  90
```

<210> SEQ ID NO 26
<211> LENGTH: 88
<212> TYPE: PRT
<213> ORGANISM: Homo sapiens

<400> SEQUENCE: 26

```
Lys Met Ser His Ile Lys Gly His Glu Gly Asp Pro Cys Leu Arg Ser
1               5                   10                  15

Ser Asp Cys Ile Glu Gly Phe Cys Cys Ala Arg His Phe Trp Thr Lys
                20                  25                  30

Ile Cys Lys Pro Val Leu His Gln Gly Glu Val Cys Thr Lys Gln Arg
            35                  40                  45
```

```
Lys Lys Gly Ser His Gly Leu Glu Ile Phe Gln Arg Cys Asp Cys Ala
    50                  55                  60
Lys Gly Leu Ser Cys Lys Val Trp Lys Asp Ala Thr Tyr Ser Ser Lys
 65                  70                  75                  80
Ala Arg Leu His Val Cys Gln Lys
                85

<210> SEQ ID NO 27
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 27

Gly Gly Gly Gly Ser
 1               5

<210> SEQ ID NO 28
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 28

Gly Gly Gly Gly Gly Gly Gly Gly Gly
 1               5

<210> SEQ ID NO 29
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 29

Glu Glu Glu Glu Glu Glu Glu Glu Glu
 1               5

<210> SEQ ID NO 30
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 30

Ser Ser Ser Ser Ser Ser Ser Ser Ser
 1               5

<210> SEQ ID NO 31
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 31

Gly Gly Gly Gly Gly Cys Pro Pro Cys
 1               5

<210> SEQ ID NO 32
<211> LENGTH: 15
<212> TYPE: PRT
<213> ORGANISM: Artificial sequence
```

```
<220> FEATURE:
<223> OTHER INFORMATION: synthetic amino acid sequence

<400> SEQUENCE: 32

Gly Gly Gly Gly Ser Gly Gly Gly Ser Gly Gly Gly Gly Ser
1               5                   10                  15

<210> SEQ ID NO 33
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 33

Ser Cys Val Pro Leu Met Arg Cys Gly Gly Cys Cys Asn
1               5                   10

<210> SEQ ID NO 34
<211> LENGTH: 14
<212> TYPE: PRT
<213> ORGANISM: Artificial sequence
<220> FEATURE:
<223> OTHER INFORMATION: synthetic amino acid sequence

<400> SEQUENCE: 34

Pro Ser Cys Val Pro Leu Met Arg Cys Gly Gly Cys Cys Asn
1               5                   10

<210> SEQ ID NO 35
<211> LENGTH: 9
<212> TYPE: PRT
<213> ORGANISM: Artificial sequence
<220> FEATURE:
<223> OTHER INFORMATION: synthetic amino acid sequence

<400> SEQUENCE: 35

Gly Asp Leu Ile Tyr Arg Asn Gln Lys
1               5

<210> SEQ ID NO 36
<211> LENGTH: 23
<212> TYPE: PRT
<213> ORGANISM: Artificial sequence
<220> FEATURE:
<223> OTHER INFORMATION: synthetic amino acid sequence

<400> SEQUENCE: 36

Gly Gly Gly Gly Gly Gly Gly Gly Pro Ser Cys Val Pro Leu Met
1               5                   10                  15

Arg Cys Gly Gly Cys Cys Asn
            20

<210> SEQ ID NO 37
<211> LENGTH: 14
<212> TYPE: PRT
<213> ORGANISM: Artificial sequence
<220> FEATURE:
<223> OTHER INFORMATION: synthetic amino acid sequence

<400> SEQUENCE: 37

Gly Ser Thr Ser Gly Ser Gly Lys Ser Ser Glu Gly Lys Gly
1               5                   10

<210> SEQ ID NO 38
<211> LENGTH: 5
```

```
<212> TYPE: PRT
<213> ORGANISM: Artificial sequence
<220> FEATURE:
<223> OTHER INFORMATION: synthetic amino acid sequence
<220> FEATURE:
<221> NAME/KEY: MISC_FEATURE
<222> LOCATION: (1)..(5)
<223> OTHER INFORMATION: the sequence may be repeated n times where n is
      an interger selected from 1, 2, 3, 4, 5, etc.

<400> SEQUENCE: 38

Gly Gly Gly Gly Ser
1               5

<210> SEQ ID NO 39
<211> LENGTH: 145
<212> TYPE: PRT
<213> ORGANISM: Bacillus halodurans

<400> SEQUENCE: 39

Met Asp Val Gln Arg Val Gly Lys Ala Gly Leu His Arg Val Asp Ser
1               5                   10                  15

Lys Lys Gln Gln Thr Ala Ala Gly Val Ser Phe Ser Glu Val Met Gly
                20                  25                  30

Lys Gln Arg Asp Glu Lys Ala Tyr Glu Arg Leu Gln Ala Leu Met Ser
            35                  40                  45

Lys Ile Asp Asp Gln Gly Lys Leu Leu Ser Glu Thr Arg Thr Ile Glu
    50                  55                  60

Glu Leu Arg Lys Tyr Lys Glu Leu Val Lys Glu Phe Val Gly Asp Ala
65                  70                  75                  80

Val Glu Leu Gly Leu Arg Leu Glu Glu Arg Arg Gly Phe Asn Arg Arg
                85                  90                  95

Gly Arg Thr Lys Ile Tyr Lys Ile Val Lys Glu Val Asp Arg Lys Leu
            100                 105                 110

Leu Asp Leu Thr Asp Ala Val Leu Ala Lys Glu Lys Lys Gly Leu Asp
        115                 120                 125

Ile Leu Asn Met Val Gly Glu Ile Lys Gly Leu Leu Ile Asn Ile Tyr
    130                 135                 140

Ala
145
```

WNT SIGNALING AGONIST MOLECULES

CROSS REFERENCE

This application is a 371 application and claims the benefit of PCT Application No. PCT/US2015/049829, filed Sep. 11, 2015, which claims benefit of U.S. Provisional Patent Application No. 62/206,150, filed Aug. 17, 2015, which claims benefit of U.S. Provisional Patent Application No. 62/049,949, filed Sep. 12, 2014. This application also claims benefit of U.S. Provisional Patent Application No. 62/345,594, filed Jun. 3, 2016. These applications are incorporated herein by reference in their entirety.

FEDERALLY SPONSORED RESEARCH AND DEVELOPMENT

This invention was made with Government support under contract GM097015 awarded by the National Institutes of Health. The Government has certain rights in the invention.

BACKGROUND OF THE INVENTION

Wnts (Wingless and Int-1) are central mediators of vertebrate and invertebrate development, due to their influences on cell proliferation, differentiation, and migration. Wnts act through activation of cell surface receptors on responder cells which activate at least three different signaling pathways including the "canonical" β-catenin pathway, and the "non-canonical" planar cell polarity (PCP) and $Ca^{2+}$ pathways.

Wnt signals can direct a wide variety of cellular responses in development, physiology, and disease. Perturbations of the Wnt pathway can lead to a variety of human diseases, ranging from birth defects to cancer. Inappropriate activation of Wnt signaling has been found in cancers, including FAP, liver cancer, skin cancer, lung cancer, Wilms' tumor, prostate cancer, and breast cancer. A variety of developmental genetic defects were also shown to occur as a result of Wnt pathway misregulation, including defects in limb formation (tetra-amelia), bone ossification, eye vascularization, and tooth development.

Wnt/β-catenin signal transduction results in the cytoplasmic protein β-catenin entering the nucleus to modulate transcription. When the pathway is not activated, β-catenin is subject to a cycle of continual synthesis and destruction by the β-catenin destruction complex, comprised of the scaffold proteins Axin and APC and the kinases GSK3 and casein kinase 1 (CK1). Wnt signaling removes APC from the complex and relocalizes the other components to the plasma membrane via the adaptor Dsh, thus stabilizing β-catenin which enters the nucleus to mediate transcription.

The seven-pass transmembrane receptor Frizzled (Fz) is critical for nearly all Wnt signaling, and the N-terminal Fz cysteine rich domain (CRD) serves as the Wnt binding domain. In addition to Fz, the Wnt/β-catenin pathway requires the Low-density lipoprotein receptor related proteins 5 and 6 (Lrp5/6) to serve as co-receptors. LRP5 and LRP6 are functionally redundant single-pass transmembrane receptors. Biochemical studies of LRP6 indicate that different Wnts may bind to different extracellular domains of the LRP5/6 protein. The LRP6 extracellular domain contains four repeating sequences of β-propeller and epidermal growth factor-like (βP-E) domains. The crystal structures of the extracellular LRP6 regions indicate that the βP-E repeats represent two discrete, compact, rigid structures, each containing two βP-E pairs. Wnt9b binds the first two βP-E repeats on the extracellular domain of LRP6, whereas Wnt3a binds the last two βP-E domains. Binding of Wnt ligands to Fz and LRP5/6 results in the production of phosphatidylinositol (4,5)-bisphosphate (PIP2). Increased PIP2 induces oligomerization and clustering of LRP5/6. Increased PIP2 induces recruitment of Axin to LRP5/6. This recruitment may be due, in part, to the action of Amer1/WTX (APC membrane recruitment 1 or Wilms tumor gene on the X chromosome), a tumor suppressor mutated in Wilms' tumor that binds to Axin, CK1γ, and GSK3. Amer1/WTX is recruited to the plasma membrane in a PIP2-dependent manner.

The interaction between LRP6 and Axin is critical for activation of the Wnt pathway, and the recruitment of Axin and the associated destruction complex to the plasma membrane upon Wnt ligand binding initiates a chain of events that leads to the phosphorylation of the intracellular domain of LRP5/6. This initial recruitment of Axin to LRP6 in a Wnt-Fz-dependent manner is referred to as the "initiation step" of Wnt pathway activation. The LRP5/6 receptor contains five PPPSPxS motifs on its intracellular domain that are required for signal transmission. Each of these five motifs alone can activate the Wnt/β-catenin pathway: when transferred to heterologous receptors, the PPPSPxS motif is sufficient for pathway activation. Mutational analyses of these motifs indicate that they act in a cooperative manner to mediate downstream signaling. Wnt binding to LRP5/6 has been shown to induce PPPSP phosphorylation. Phosphorylated LRP6 has a high affinity for Axin and promotes further recruitment of cytoplasmic Axin-bound GSK3 complexes to the cell surface. Once the Axin-bound β-catenin destruction complex is recruited by LRP6, the phosphorylated cytoplasmic domain of LRP6 is capable of directly inhibiting GSK3 activity, blocking β-catenin phosphorylation and subsequent ubiquitin-mediated proteasomal degradation.

Non-Wnt agonists include Norrin and R-Spondin. Norrin is a Fz4-specific ligand that, in complex with LRP5. The four R-Spondin genes represent a family of conserved secreted proteins that potentiate the Wnt pathway. LGR4/5/6 (leucine-rich repeat-containing GPCRs 4, 5, and 6) are receptors for R-Spondins. The role of R-Spondins appears to stabilize the Wnt receptors, Fz and LRP6, to promote Wnt signaling.

Recently, the type 1 transmembrane protein, Tiki, was identified in an expression cloning screening for mRNAs that perturbed axis formation in *X. laevis* embryos (Zhang et al. 2012). Tiki was shown to be a novel metalloprotease that cleaved the N-terminal 8 amino acids of mature Wnt proteins. In vitro, Tiki-mediated cleavage of this N-terminal fragment of Wnts results in the formation of soluble, large oligomeric Wnt complexes due to oxidation and formation of disulfide bonds. Whether or not formation of these large, inactive proteolyzed Wnt complexes is the mechanism of action of Tiki in the Wnt pathway in vivo remains to be elucidated.

The development of pharmaceutically active wnt compositions that are water soluble is therefore of great interest.

SUMMARY OF THE INVENTION

Wnt signaling agonist molecules and methods for their use are provided. The molecules of the invention are water soluble; bind with high affinity to both (i) frizzled (Fzd) proteins and (ii) Lrp5/6; and directly activate canonical wnt pathway signaling. The wnt signaling agonist molecules act as agonists of Fzd, and find use in methods of activating wnt pathway signaling. In some embodiments the wnt signaling agonist molecules bind to human Fzd and Lrp5/6 proteins. Molecules of the invention include, without limitation, small organic molecules and polypeptides.

In some embodiments of the invention, the wnt signaling agonist molecule is a polypeptide, which can comprise separate or contiguous binding domains or elements for Fzd, and for Lrp5/6. A polypeptide wnt signaling agonist may be a single chain, dimer, or higher order multimer. The Fzd binding domain/element and the Lrp5/6 binding domain/element may be directly joined, or may be separated by a linker, e.g. a polypeptide linker, or a non-peptidic linker, etc.

In polypeptide embodiments, the Fzd binding domain may be selected from any domain that binds Fzd at high affinity, e.g. a KD of at least about $1 \times 10-7$ M, at least about $1 \times 10-8$ M, at least about $1 \times 10-9$ M, or at least about $1 \times 10-10$ M. Suitable Fzd binding domains include, without limitation, de novo designed Fzd binding proteins, antibody derived binding proteins, e.g. scFv, Fab, etc. and other portions of antibodies that specifically bind to one or more Fzd proteins; nanobody derived binding domains; knottin-based engineered scaffolds; norrin and engineered binding fragments derived therefrom, naturally occurring Fzd binding domains, and the like. A Fzd binding domain may be affinity selected to enhance binding to a desired Fzd protein or plurality of Fzd proteins, e.g. to provide tissue selectivity.

In some embodiments the Fzd binding domain binds to one, two, three, four, five or more different frizzled proteins, e.g. one or more of human frizzled proteins Fz1, Fz2, Fz3, Fz4, Fz5, Fz6, Fz7, Fz8, Fz9, Fz10. In some embodiments the antibody based signaling agonist binds to Fz1, Fz2, Fz5, Fz7 and Fz8. In other embodiments the frizzled binding moiety is selective for one or more frizzled protein of interest, e.g. having a specificity for the one or more desired frizzled protein of at least 10-fold, 25-fold, 50-fold, 100-fold, 200-fold or more relative to other frizzled proteins.

In polypeptide embodiments, the Lrp5/6 binding domain or element may be selected from any domain that binds Lrp5/6 at high affinity, e.g. a $K_D$ of at least about $1 \times 10^{-7}$ M, at least about $1 \times 10^{-8}$ M, at least about $1 \times 10^{-9}$ M, at least about $1 \times 10^{-10}$ M. Suitable Lrp5/6 binding domains include, without limitation, de novo designed Lrp5/6 binding proteins, antibody derived binding proteins, e.g. scFv, Fab, etc. and other portions of antibodies that specifically bind to one or more Fzd proteins; nanobody derived binding domains; knottin-based engineered scaffolds; naturally occurring Lrp5/6 binding proteins or polypeptides, including without limitation, Norrin, DKK1, DKK2, DKK3, DKK4, sclerostin; and the like. In certain embodiments the Lrp5/6 binding domain is a c-terminal portion of DKK1. A Lrp5/6 binding domain may be affinity selected to enhance binding.

A wnt signaling agonist polypeptide can be fused, linked, or alternatively co-administered with an agent to enhance wnt activation. Polypeptides that enhance wnt activity include, without limitation, R-spondin 1, R-spondin 2, anti-sclerosin antibody, etc.

A wnt signaling agonist polypeptide can be fused, linked or alternatively co-administered with a growth factor of interest, including growth factors active of bone growth, skin regeneration, stem cell activation, and the like.

The Fzd binding domain and the Lrp5/6 binding domain may be contiguous within one globular domain, or separated by a linker, e.g. a polypeptide linker, or a non-peptidic linker, etc. The length of the linker, and therefore the spacing between the binding domains can be used to modulate the signal strength, and can be selected depending on the desired use of the wnt signaling agonist. The enforced distance between binding domains can vary, but in certain embodiments may be less than about 100 angstroms, less than about 90 angstroms, less than about 80 angstroms, less than about 70 angstroms, less than about 60 angstroms, or less than about 50 angstroms.

In some embodiments the linker is a rigid linker, in other embodiments the linker is a flexible linker. Where the linker is a peptide linker, it may be from about 1, 2, 3, 4, 5, 6, 7, 8, 9, 10, 11, 12, 13, 14, 15, 16, 17, 18, 19, 20 21, 22, 23, 24, 25, 26, 27, 28, 29, 30 or more amino acids in length, and is of sufficient length and amino acid composition to enforce the distance between binding domains. In some embodiments the linker comprises or consists of one or more glycine and/or serine residues.

A wnt signaling agonist can be multimerized, e.g. through an Fc domain, by concatenation, coiled coils, polypeptide zippers, biotin/avidin or streptavidin multimerization, and the like. The wnt signaling agonist can also be joined to a moiety such as PEG, Fc, etc. as known in the art to enhance stability in vivo.

Compositions of interest include, without limitation, an effective dose of a wnt signaling agonist in a pharmaceutically acceptable excipient. Compositions may comprise additional agents, e.g. adjuvants and the like. Wnt signaling agonists may be produced synthetically; by various suitable recombinant methods, and the like, as known in the art. In addition, a benefit of the water soluble forms of wnt signaling agonists is the lack of a requirement for formulation additives, e.g. lipids, detergents, etc. that might limit their therapeutic utility.

In some aspects of the invention, a method is provided for activating, increasing or enhancing Wnt signaling in a cell. In such methods, a cell expressing a frizzled receptor is contacted with a concentration of a wnt signaling agonist that is effective to increase signaling, e.g. to increase signaling by 25%, 50%, 75%, 90%, 95%, or more, relative to the signaling in the absence of the wnt signaling agonist. Such signaling activation may induce proliferation of the targeted cell, which cells include without limitation stem cells, or may otherwise activate Wnt-signaling pathways in the targeted cell. In some methods, the receptor-expressing cell is contacted in vitro. In other embodiments, the receptor-expressing cell is contacted in vivo. Cells of interest include a wide variety of Fzd-receptor expressing cells, as are known in the art, for example skin cells, intestinal cells, osteoblasts, stem cells, etc.

In some aspects of the invention, a method is provided for treating or preventing a disease or disorder in a subject in need thereof, the method comprising providing to the subject an effective amount of a wnt signaling agonist. In particular embodiments, the subject has a disease or disorder associated with reduced wnt signaling.

In some aspects of the invention, a method is provided for enhancing wound healing and/or tissue generation in a subject in need thereof, the method comprising providing to the subject an effective amount of a wnt signaling agonist. A benefit of the compositions and methods of the invention is the specificity of targeting and the water solubility of the signaling agonist, where the wnt signaling agonist can targets the same cells as a native wnt protein, or can selectively activate wnt signaling in desired tissue.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 5. Provides the amino acid sequence (SEQ ID NO:10) of an exemplary surrogate wnt agonist, depicting the scFv domain, and the Lrp5/6 binding domain. The scFv (Onco)-DKK1c, comprises the scFv fragment of the OMP-18R5 antibody (Oncomed), labeled as the variable region of the light chain and variable region of the light chain, joined by linker 1, and the C-terminal domain of human DKK-1, covalently linked by a flexible polypeptide linker 2. The sequence shown has SEQ ID NO: 10.

FIG. 8A-8C. Frizzled-subtype specific activation of the Wnt dependent pBAR reporter by the surrogate ligands in: (FIG. 8A) non-small cell lung cancer cell line A549 pBAR (FIG. 8B) melanoma cell line A375 pBAR and (FIG. 8C) neural blastoma cell line SY5Y pBAR. Activity of the scFv-DKK1c and B12-DKK1c surrogate ligands, XWnt8, B12, DKK1, and unrelated proteins to induce the expression of the pBAR reporter was measured at various different concentrations (indicated underneath the diagram). Enhanced reporter expression correlates with Frizzled specificity of surrogate Wnt agonist, and the Frizzled expression profiles of the corresponding cells determined by qRT-RCR. Frizzled reactivities of scFv-DKK1c, B12-DKK1c and XWnt8 are indicated on the table, Frizzled expression profiles of the corresponding cells were determined by qRT-PCR and are indicated with boxes as marked, and Wnt reporter activation with corresponding ligands are indicated with boxes as marked in the tables underneath the diagrams. The sequence shown in FIG. 8C has SEQ ID NO: 20.

(FIG. 9A) While scFv(Onco)-DKK1c activates the expression of the Wnt-signaling dependent luciferase reporter in L-cells, which predominantly express Frizzled 7, these cells are not responsive to the Fzd5/8 specific B12-DKK1c surrogate ligand and XWnt8, or isolated B12, and DKK-1. (FIG. 9B/9C) the activity of B12-DKK1c and XWnt8 in L-cells can be rescued by over-expression of Frizzled 5 and Frizzled 8 by transient transfection.

FIG. 13A-13B. Varying the length of the flexible linker of the surrogate Wnt ligands, and thereby the geometry of Frizzled/Lrp5/6 dimerization, alters the signaling amplitude as observed by Wnt-target gene transcription (FIG. 13A) and expression of the Wnt-signaling dependent luciferase reporter (FIG. 13B). A), A549 pBAR cells in the presence of 2 M IWP-2 were treated with 50 nM XWnt8, 50 nM B12-DKK1c with 0 aa, 5aa, 10aa and 15aa linkers, or 30% Wnt3a-L conditioned medium for 24 hrs. mRNA was extracted, reverse transcribed to cDNA, and qRT-PCR was used to detect levels of the Wnt target gene Axin2 transcript. FIG. 13B), The amplitude of reporter activation in A549 pBAR cells by increasing concentration of XWnt8 and B12-DKK1c variants with variable linker length was assessed in the presence of 2 uM IWP-2 as described in FIG. 4. The sequences shown in FIG. 13A have, from top to bottom, the SEQ ID NO: 20-22.

FIG. 15. R-spondin 2 strongly potentiates activity of scFv(Onco)-DKK1c to induce the expression of the Wnt-signaling dependent SuperTopFlash reporter in HEK293 cells, and to a comparable level as Wnt3a. HEK293 cells stably transfected with the SuperTopFlash Wnt reporter were treated for 16-20 hrs with scFv(Onco)-DKK1c (4 nM, 8 nM, 16 nM, 31 nM, 62 nM) Wnt3a (23% 29%, 33%, 38%, 41%, 44%) with and without 20 nM Rspo2 for 16-20 hrs. Enhanced luciferase activity was detected with the Dual-Luciferase reporter assay system. The sequence shown has SEQ ID NO: 19.

DETAILED DESCRIPTION OF THE INVENTION

Figure 1:
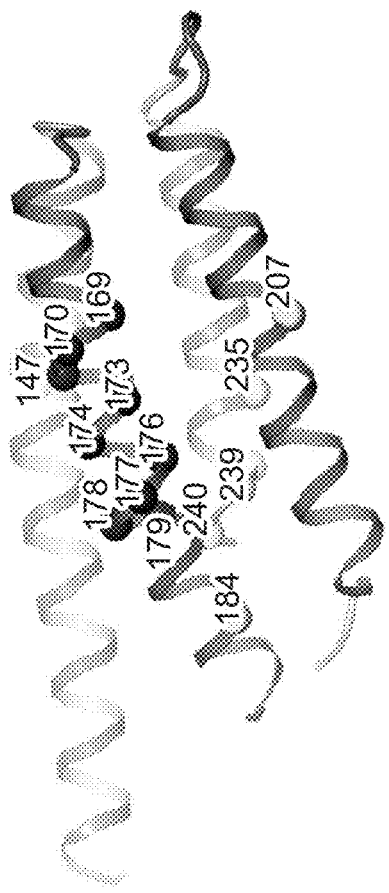
FIG. 1. Interface, core and structural residues in the designed Fzd27 variant that contribute to affinity maturation. The sequences shown are, in order from top to bottom SEQ ID NO: 11-18.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

By "comprising" it is meant that the recited elements are required in the composition/method/kit, but other elements may be included to form the composition/method/kit etc. within the scope of the claim. For example, a composition comprising a wnt surrogate is a composition that may comprise other elements in addition to wnt surrogate(s), e.g. functional moieties such as polypeptides, small molecules, or nucleic acids bound, e.g. covalently bound, to the wnt surrogate; agents that promote the stability of the wnt surrogate composition, agents that promote the solubility of the wnt surrogate composition, adjuvants, etc. as will be readily understood in the art, with the exception of elements that are encompassed by any negative provisos.

By "consisting essentially of", it is meant a limitation of the scope of composition or method described to the specified materials or steps that do not materially affect the basic and novel characteristic(s) of the subject invention. For example, a wnt surrogate "consisting essentially of" a disclosed sequence has the amino acid sequence of the disclosed sequence plus or minus about 5 amino acid residues at the boundaries of the sequence based upon the sequence from which it was derived, e.g. about 5 residues, 4 residues, 3 residues, 2 residues or about 1 residue less than the recited bounding amino acid residue, or about 1 residue, 2 residues, 3 residues, 4 residues, or 5 residues more than the recited bounding amino acid residue.

By "consisting of", it is meant the exclusion from the composition, method, or kit of any element, step, or ingredient not specified in the claim. For example, a wnt surrogate "consisting of" a disclosed sequence consists only of the disclosed amino acid sequence.

By "functional moiety" or "FM" it is meant a polypeptide, small molecule or nucleic acid composition that confers a functional activity upon a composition. Examples of functional moieties include, without limitation, therapeutic moieties, binding moieties, and imaging moieties.

By "therapeutic moiety", or "TM", it is meant a polypeptide, small molecule or nucleic acid composition that confers a therapeutic activity upon a composition. Examples of therapeutic moieties include cytotoxins, e.g. small molecule compounds, protein toxins, and radiosensitizing moieties, i.e. radionuclides etc. that are intrinsically detrimental to a cell; agents that alter the activity of a cell, e.g. small molecules, peptide mimetics, cytokines, chemokines; and moieties that target a cell for ADCC or CDC-dependent death, e.g. the Fc component of immunoglobulin.

By an "imaging moiety", or "IM", it is meant a non-cytotoxic agent that can be used to locate and, optionally, visualize cells, e.g. cells that have been targeted by compositions of the subject application.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy may be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired, particularly humans.

General methods in molecular and cellular biochemistry can be found in such standard textbooks as Molecular Cloning: A Laboratory Manual, 3rd Ed. (Sambrook et al., CSH Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and Clon-Tech.

Compositions

Wnt signaling agonists, also referred to herein as surrogate molecules, and methods for their use are provided. These and other objects, advantages, and features of the invention will become apparent to those persons skilled in the art upon reading the details of the compositions and methods as more fully described below.

A Wnt surrogate molecule is defined by its physical and biological properties. Key features are water solubility, and the direct activation of canonical wnt signaling through binding to one or more Fzd proteins and to Lrp5/6, particularly by binding to these proteins on a cell surface, e.g. the surface of a human cell. The direct activation of wnt signaling by a wnt surrogate is in contrast to potentiation of wnt signaling, which enhances activity only when native wnt proteins are present.

A wnt surrogate can be any molecule, e.g. protein or pharmaceutical, with the properties of water solubility, and the direct activation of canonical wnt signaling through binding to one or more Fzd proteins and to Lrp5/6. Small molecules, which may be less than about 15 Kd, are of interest and can be developed through compound screening as described herein. Polypeptides are also of interest. In addition, certain wnt surrogates may comprise both a polypeptide region or domain and a non-polypeptide region or domain.

A wnt surrogate can be a polypeptide, where a binding domain for Fzd is joined to a binding domain for Lrp5/6. A polypeptide wnt surrogate may be a single chain, dimer, or higher order multimer. The Fzd binding domain and the Lrp5/6 binding domain may be directly joined, or may be separated by a linker, e.g. a polypeptide linker, or a non-peptidic linker, etc.

Wnt surrogates of the present invention are usually biologically active in binding to a cognate Frizzled receptor, and in activation of wnt signaling, i.e. the surrogate is a wnt agonist. The term "wnt agonist activity" refers to the ability of an agonist to mimic the effect or activity of a wnt protein binding to a frizzled protein. The ability of the agonists of the invention to mimic the activity of wnt can be confirmed by a number of assays. The agonists of the invention typically initiate a reaction or activity that is similar to or the same as that initiated by the receptors natural ligand. In particular, the agonists of the invention enhance the canonical Wnt/β-catenin signaling pathway. As used herein, the term "enhances" refers to a measurable increase in the level of Wnt/β-catenin signaling compared with the level in the absence of an agonist of the invention.

Various methods are known in the art for measuring the level of canonical Wnt/β-catenin signaling. These include, but are not limited to assays that measure: Wnt/β-catenin target gene expression; TCF reporter gene expression; beta-catenin stabilization; LRP phosphorylation; Axin translocation from cytoplasm to cell membrane and binding to LRP. The canonical Wnt/β-catenin signaling pathway ultimately leads to changes in gene expression through the transcription factors TCF7, TCF7L1, TCF7L2 and LEF. The transcriptional response to Wnt activation has been characterized in a number of cells and tissues. As such, global transcriptional profiling by methods well known in the art can be used to assess Wnt/β-catenin signaling activation.

Changes in wnt-responsive gene expression are generally mediated by TCF and LEF transcription factors. A TCF reporter assay assesses changes in the transcription of TCF/LEF controlled genes to determine the level of Wnt/.beta.-catenin signaling. A TCF reporter assay was first described by Korinek, V. et al., 1997. Also known as TOP/FOP this method involves the use of three copies of the optimal TCF motif CCTTTGATC, or three copies of the mutant motif CCTTTGGCC, upstream of a minimal c-Fos promoter driving luciferase expression (pTOPFLASH and pFOPFLASH, respectively) to determine the transactivational activity of endogenous β-catenin/TCF4. A higher ratio of these two reporter activities (TOP/FOP) indicates higher β-catenin/TCF4 activity.

Various other reporter transgenes that respond to Wnt signals exist intact in animals and therefore, effectively reflect endogenous Wnt signaling. These reporters are based on a multimerized TCF binding site, which drives expression of LacZ or GFP, which are readily detectable by methods known in the art. These reporter genes include: TOP-GAL, BAT-GAL, ins-TOPEGFP, ins-TOPGAL, LEF-EGFP, Axin2-LacZ, Axin2-d2EGFP, Lgr5tm1(cre/ERT2), TOPdGFP.

The recruitment of dephosphorylated β-catenin to the membrane, stabilisation and phosphorylation status of β-catenin and translocation of β-catenin to the nucleus (Klapholz-Brown Z et al., PLoS One. 2(9) e945, 2007) in some cases mediated by complex formation with TCF transcription factors and TNIK are key steps in the Wnt signaling pathway. Stabilisation is mediated by Disheveled family proteins that inhibit the "destruction" complex so that degradation of intracellular β-catenin is reduced, and translocation of β-catenin to the nucleus follows thereafter. Therefore, measuring the level and location of β-catenin in a cell is a good reflection of the level of Wnt/β-catenin signaling. A non-limiting example of such an assay is the "BioImage β-Catenin Redistribution Assay" (Thermo Scientific) which provides recombinant U2OS cells that stably express human β-catenin fused to the C-terminus of enhanced green fluorescent protein (EGFP). Imaging and analysis is performed with a fluorescence microscope or HCS platform allowing the levels and distribution of EGFP-β-catenin to be visualized.

Another way, in which the destruction complex is inhibited, is by removal of Axin by recruitment of Axin to the cytoplasmic tail of the Wnt co-receptor LRP. Axin has been shown to bind preferentially to a phosphorylated form of the LRP tail. Visualisation of Axin translocation, for example with a GFP-Axin fusion protein, is therefore another method for assessing levels of Wnt/β-catenin signaling.

In certain embodiments, the surrogates of the invention may enhance β-catenin signaling by at least 30%, 35%, 40%, 45%, 50%, 60%, 70%, 75%, 80%, 85%, 90%, 95%, 100%, 110%, 150%, 200%, 250%, 300%, 400% or 500% compared to the β-catenin signaling induced by a neutral substance or negative control as measured in an assay described above, for example as measured in the TOPFlash assay. A negative control may be included in these assays. In particular embodiments, the surrogates of the invention may enhance β-catenin signaling by a factor of 2×, 5×, 10×, 100×, 1000×, 10000× or more as compared to the activity in the absence of the agonist when measured in an assay described above, for example when measured in the TOP-Flash assay, or any of the other assays mentioned herein.

"Wnt gene product" or "Wnt polypeptide" when used herein encompass native sequence Wnt polypeptides, Wnt polypeptide variants, Wnt polypeptide fragments and chimeric Wnt polypeptides. In particular embodiments, a Wnt polypeptide is a native human full length mature Wnt protein.

For example, human native sequence Wnt proteins of interest in the present application include the following: Wnt-1 (GenBank Accession No. NM_005430); Wnt-2 (GenBank Accession No. NM_003391); Wnt-2B (Wnt-13) (GenBank Accession No. NM_004185 (isoform 1), NM_024494.2 (isoform 2)), Wnt-3 (RefSeq.: NM_030753), Wnt3a (GenBank Accession No. NM_033131), Wnt-4 (GenBank Accession No. NM_030761), Wnt-5A (GenBank Accession No. NM_003392), Wnt-5B (GenBank Accession No. NM_032642), Wnt-6 (GenBank Accession No. NM_006522), Wnt-7A (GenBank Accession No. NM_004625), Wnt-7B (GenBank Accession No. NM_058238), Wnt-8A (GenBank Accession No. NM_058244), Wnt-8B (GenBank Accession No. NM_003393), Wnt-9A (Wnt-14) (GenBank Accession No. NM_003395), Wnt-9B (Wnt-15) (GenBank Accession No. NM_003396), Wnt-10A (GenBank Accession No. NM_025216), Wnt-10B (GenBank Accession No. NM_003394), Wnt-11 (GenBank Accession No. NM_004626), Wnt-16 (GenBank Accession No. NM_016087)). Although each member has varying degrees of sequence identity with the family, all encode small (i.e., 39-46 kD), acylated, palmitoylated, secreted glycoproteins that contain 23-24 conserved cysteine residues whose spacing is highly conserved (McMahon, A P et al., Trends Genet. 1992; 8: 236-242; Miller, J R. Genome Biol. 2002; 3(1): 3001.1-3001.15). Other native sequence Wnt polypeptides of interest include orthologs of the above from any mammal, including domestic and farm animals, and zoo, laboratory or pet animals, such as dogs, cats, cattle, horses, sheep, pigs, goats, rabbits, rats, mice, frogs, zebra fish, fruit fly, worm, etc.

"Wnt protein signaling" or "Wnt signaling" is used herein to refer to the mechanism by which a biologically active Wnt exerts its effects upon a cell to modulate a cell's activity. Wnt proteins modulate cell activity by binding to Wnt receptors, including proteins from the Frizzled (Fz) family of proteins, proteins from the ROR family of proteins, the proteins LRP5, LRP6 from the LRP family of proteins, the protein FRL1/crypto, and the protein Derailed/Ryk. Once activated by Wnt binding, the Wnt receptor(s) will activate one or more intracellular signaling cascades. These include the canonical Wnt signaling pathway; the Wnt/planar cell polarity (Wnt/PCP) pathway; the Wnt-calcium (Wnt/Ca$^{2+}$) pathway (Giles, R H et al. (2003) Biochim Biophys Acta 1653, 1-24; Peifer, M. et al. (1994) Development 120: 369-380; Papkoff, J. et al (1996) Mol. Cell Biol. 16: 2128-2134; Veeman, M. T. et al. (2003) Dev. Cell 5: 367-377); and other Wnt signaling pathways as is well known in the art.

For example, activation of the canonical Wnt signaling pathway results in the inhibition of phosphorylation of the intracellular protein β-catenin, leading to an accumulation of β-catenin in the cytosol and its subsequent translocation to the nucleus where it interacts with transcription factors, e.g. TCF/LEF, to activate target genes. Activation of the Wnt/PCP pathway activates RhoA, c-Jun N-terminal kinase (JNK), and nemo-like kinase (NLK) signaling cascades to control such biological processes as tissue polarity and cell movement. Activation of the Wnt/Ca$^{2+}$ by, for example, binding of Wnt-4, Wnt-5A or Wnt-11, elicits an intracellular release of calcium ions, which activates calcium sensitive enzymes like protein kinase C (PKC), calcium-calmodulin dependent kinase II (CamKII) or calcineurin (CaCN). By assaying for activity of the above signaling pathways, the biological activity of a Wnt composition can be readily determined. A "biologically active wnt surrogate" is a wnt surrogate composition that is able to specifically bind to a Fzd receptor and activate Wnt signaling when provided to a cell in vitro or in vivo, that is, when administered to an animal, e.g. a mammal.

In certain embodiments, a wnt surrogate of the invention increases signaling of the canonical wnt pathway by at least about 50%, about 75%, about 100%, about 150%, about 200%, about 300%, about 400%, about 5-fold, about 10-fold, and may increase signaling by 50-fold, 100-fold, 500-fold, or more, relative to the level of wnt signaling in the absence of the surrogate.

The term "specific binding" refers to that binding which occurs between such paired species as enzyme/substrate, receptor/ligand, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or ligand/receptor interaction. One may determine the biological activity of a wnt surrogate in a composition by determining the level of activity in a functional assay after in vivo administration, e.g. accelerating bone regeneration, enhancing stem cell proliferation, etc., nuclear localization of β-catenin, increased transcription of wnt-responsive genes; etc.

By "water soluble" it is meant a composition that is soluble in aqueous buffers in the absence of detergent, usually soluble at a concentration that provides a biologically effective dose of the polypeptide. Compositions that are water soluble form a substantially homogenous composition that has a specific activity that is at least about 5% that of the starting material from which it was purified, usually at least about 10%, 20%, or 30% that of the starting material, more usually about 40%, 50%, or 60% that of the starting material, and may be about 50%, about 90% or greater. Wnt surrogate compositions of the present invention typically form a substantially homogeneous aqueous solution at concentrations of at least 25 μM and higher, e.g. at least 25 μM, 40 μM, or 50 μM, usually at least 60 μM, 70 μM, 80 μM, or 90 μM, sometimes as much as 100 μM, 120 μM, or 150 μM. In other words, wnt surrogate compositions of the present invention typically form a substantially homogeneous aqueous solution at concentrations of about 0.1 mg/ml, about 0.5 mg/ml, of about 1 mg/ml or more.

Fzd Binding Domain.

The Fzd binding domain may be a small molecule or a polypeptide, and can be selected from any domain that binds Fzd at high affinity, e.g. a $K_D$ of at least about $1\times10^{-7}$ M, at least about $1\times10^{-8}$ M, at least about $1\times10^{-9}$ M, at least about $1\times10^{-10}$ M. Suitable Fzd binding domains include, without limitation, de novo designed Fzd binding proteins, antibody derived binding proteins, e.g. scFv, Fab, etc. and other portions of antibodies that specifically bind to one or more Fzd proteins; nanobody derived binding domains; knottin-based engineered scaffolds; norrin and binding fragments derived therefrom; and the like.

A Fzd binding domain may be affinity selected to enhance binding to a desired Fzd protein or plurality of Fzd proteins, e.g. to provide tissue selectivity. Methods of affinity selection for this purpose may optionally utilize one or more rounds of selection by introducing targeted amino acid changes and generating a library of candidate coding sequences, transforming a population of cells with the candidate coding sequence, e.g. into yeast cells, selecting (for example using paramagnetic microbeads) for the desired specificity. Typically multiple rounds of selection will be performed, and the resulting vectors sequenced and used as the basis for protein engineering. For example, the Fzd binding domain, including without limitation a norrin binding domain, an antibody or nanobody derived domain, an engineered protein, etc. can be selected to bind selectively to one or more Fzd proteins of interest. For example, norrin can be affinity selected to bind to a Fzd receptor other than, or in addition to, Fzd4.

In some embodiments the Fzd binding domain binds to one, two, three, four, five or more different frizzled proteins, e.g. one or more of human frizzled proteins Fz1, Fz2, Fz3, Fz4, Fz5, Fz6, Fz7, Fz8, Fz9, Fz10. In some embodiments, the antibody based surrogate binds to Fz1, Fz2, Fz5, Fz7 and Fz8. In other embodiments the frizzled binding moiety is selective for one or more frizzled protein of interest, e.g. having a specificity for the one or more desired frizzled protein of at least 10-fold, 25-fold, 50-fold, 100-fold, 200-fold or more relative to other frizzled proteins.

In certain embodiments, the frizzled binding domain comprises the six CDR regions of the pan specific frizzled antibody OMP-18R5 (vantictumab). In certain embodiments, the frizzled binding domain is an scFv comprising the six CDR regions of the pan-specific frizzled antibody OMP-18R5 (vantictumab). See, for example, U.S. Pat. No. 8,507,442, herein specifically incorporated by reference. For example, the CDR sequences of OMP-18R5 include a heavy chain CDR1 comprising GFTFSHYTLS (SEQ ID NO:1), a heavy chain CDR2 comprising VISGDGSYTYYADSVKG (SEQ ID NO:2), and a heavy chain CDR3 comprising NFIKYVFAN (SEQ ID NO:3), and (ii) a light chain CDR1 comprising SGDKLGKKYAS (SEQ ID NO:4) or SGD-NIGSFYVH (SEQ ID NO:7), a light chain CDR2 comprising EKDNRPSG (SEQ ID NO:5) or DKSNRPSG (SEQ ID NO:8), and a light chain CDR3 comprising SSFAGNSLE (SEQ ID NO:6) or QSYANTLSL (SEQ ID NO:9). In particular embodiments, the frizzled binding domain is an antibody or derivative thereof, including without limitation ScFv, minibodies, nanobodies and various antibody mimetics comprising the CDR sequences of SEQ ID NOs:1-9. In certain embodiments, these CDR sequences comprise one or more amino acid modifications as compared to SEQ ID NOs:1-9.

In other embodiments, the Fzd binding domain comprises a variable region sequence, or the CDRs thereof, from any of a number of frizzled specific antibodies, which are known in the art and are commercially available, or can be generated de novo. Any of the frizzled polypeptides can be used as an immunogen or in screening assays to develop an antibody. "Fz", "Fz proteins" and "Fz receptors" is used herein to refer to proteins of the Frizzled receptor family. These proteins are seven-pass transmembrane proteins (Ingham, P. W. (1996) Trends Genet. 12: 382-384; Yang-Snyder, J. et al. (1996) Curr. Biol. 6: 1302-1306; Bhanot, P. et al. (1996) Nature 382: 225-230) that comprise a CRD domain. There are ten known members of the Fz family (Fz1 through Fz10), any of which can serve as receptors of Wnts. The Genbank accession numbers of human frizzled reference sequences are as follows: FZD1 (NM_003505); FZD2 (NM_001466); FZD3 (NM_145866); FZD4 (NM_012193); FZD5 (NM_003468); FZD6 (NM_003506); FZD7 (NM_003507); FZD8 (NM_031866); FZD9 (NM_003508); FZD10 (NM_007197).

Non-limiting examples of frizzled binding domains include antibodies available from Biolegend, e.g. Clone CH3A4A7 specific for human frizzled 4 (CD344); Clone W3C4E11 specific for human Fz9 (CD349); antibodies available from Abcam, e.g. ab64636 specific for Fz7; ab83042 specific for human Fz4; ab77379 specific for human Fz7; ab75235 specific for human Fz8; ab102956 specific for human Fz9; and the like. Other examples of suitable antibodies are described in, inter alia, US Patent application 20140105917; US Patent application 20130230521; US Patent application 20080267955; US Patent application 20080038272; US Patent application 20030044409; etc., each herein specifically incorporated by reference.

The frizzled binding moiety of the surrogate may be an engineered protein that is selected for structural homology to the frizzled binding region of a wnt protein. Such proteins can be identified by screening a structure database for homologies. The initial protein thus identified, for example the microbial Bh1478 protein. The native protein is then engineered to provide amino acid substitutions that increase affinity, and may further be selected by affinity maturation for increased affinity and selectivity in binding to the desired frizzled protein. Non-limiting examples of frizzled binding moieties include the Fz27 and Fz27-B12 proteins illustrated in FIG. 1.

Lrp5/6 Binding Domain.

An Lrp5/6 may be selected from any domain that binds Lrp5 or Lrp6 at high affinity, e.g. with a $K_D$ of at least about $1\times10^{-7}$ M, at least about $1\times10^{-8}$ M, at least about $1\times10^{-9}$ M, at least about $1\times10^{-10}$ M.

"LRP", "LRP proteins" and "LRP receptors" is used herein to refer to proteins of the low density lipoprotein receptor-related protein family. These receptors are single-pass transmembrane proteins that bind and internalize ligands in the process of receptor-mediated endocytosis. LRP proteins LRP5 (GenBank Accession No. NM 002335.2) and LRP6 (GenBank Accession No. NM 002336.2) are included in the Wnt receptor complex.

Suitable Lrp5/6 binding domains include, without limitation, de novo designed Lrp5/6 binding proteins, antibody derived binding proteins, e.g. scFv, Fab, etc. and other portions of antibodies that specifically bind to one or more Fzd proteins; nanobody derived binding domains; knottin-based engineered scaffolds; naturally occurring Lrp5/6, including without limitation, DKK1, DKK2, DKK3, DKK4, sclerostin; Wise; fusions proteins comprising any of the above; derivatives of any of the above; variants of any of the above; and biologically active fragments of any of the above, and the like. A Lrp5/6 binding domain may be affinity selected to enhance binding.

Members of the Dickkopf (Dkk) gene family (see Krupnik et al. (1999) Gene 238(2):301-13) include Dkk-1, Dkk-2, Dkk-3, and Dkk-4, and the Dkk-3 related protein Soggy (Sgy). hDkks 1-4 contain two distinct cysteine-rich domains in which the positions of 10 cysteine residues are highly conserved between family members. Exemplary sequences of human Dkk genes and proteins are publicly available, e.g. Genbank accession number NM_014419 (soggy-1); NM_014420 (DKK4); AF177394 (DKK-1); AF177395 (DKK-2); NM_015881 (DKK3); and NM_014421 (DKK2). In some embodiments of the invention, the Lrp6 binding moiety is a DKK1 peptide, including without limitation the C-terminal domain of human DKK1. As shown in FIG. 5, the C-terminal domain may comprise the sequence KMYHTKGQEGSVCLRSSDCASGLCCA-RHFWSKICKPVLKEGQVCTKHRRKGSHGLEI FQR-CYCGEGLSCRIQKDHHQASNSSRLHTCQRH (SEQ ID NO: 25) (see Genbank accession number NP_036374) or a biologically active fragment thereof.

Binding of DKK proteins to LRP5/6 are discussed, for example in Brott and Sokol Mol. Cell. Biol. 22 (17), 6100-6110 (2002); and Li et al. J. Biol. Chem. 277 (8), 5977-5981 (2002), each herein specifically incorporated by reference. The corresponding region of human DKK2 (Genbank reference NP_055236) may comprise the sequence KMSHIKGHEGDPCLRSSDCIEGFCCARHFWTKICK-PVLHQGEVCTKQRKKGSHGLEIF QRCDCAKGLSC-KVWKDATYSSKARLHVCQK (SEQ ID NO: 26) or a biologically active fragment thereof.

Antibodies that specifically bind to Lrp5 or Lrp6 are known in the art and are commercially available, or can be generated de novo. Lrp5, Lrp6 or fragments thereof can be used as an immunogen or in screening assays to develop an antibody. Examples of known antibodies include, without limitation, those described in Gong et al. (2010) PLoS One. 5(9):e12682; Ettenberg et al. (2010) Proc Natl Acad Sci USA. 107(35):15473-8; and those commercially available from, for example Santa Cruz biotechnology antibody clone 1A12, which was raised against synthetic LRP5/6 of human origin and binds to both the full length and proteolytic fragment of LRP 6 and LRP 5 of mouse and human origin; the monoclonal antibody 2611; Cell Signaling Technology antibody specific for LRP5 (D80F2), catalog number 5731; etc.

Variants.

Binding domains may also include derivatives, variants, and biologically active fragments of polypeptides described above. A "variant" polypeptide means a biologically active polypeptide as defined below having less than 100% sequence identity with a provided sequence. Such variants include polypeptides comprising one or more amino acid modifications, e.g., insertions, deletions or substitutions, as compared to the provided sequence, e.g., wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%.

A "functional derivative" of a sequence is a compound having a qualitative biological property in common with an initial sequence. "Functional derivatives" include, but are not limited to, fragments of a sequence and derivatives of a sequence, provided that they have a biological activity in common. The term "derivative" encompasses both amino acid sequence variants of polypeptide and covalent modifications thereof.

Wnt surrogates for use in the subject compositions and methods may be modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The wnt surrogates may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like. If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

A wnt surrogate may be fused or bonded to an additional polypeptide sequence. Examples include immunoadhesins, which combine a wnt surrogate with an immunoglobulin sequence particularly an Fc sequence, and epitope tagged polypeptides, which comprise a native inhibitors polypeptide or portion thereof fused to a "tag polypeptide". The tag polypeptide has enough residues to provide an epitope against which an antibody can be made, yet is short enough such that it does not interfere with biological activity of the native inhibitors polypeptide. Suitable tag polypeptides generally have at least six amino acid residues and usually between about 6-60 amino acid residues. The wnt surrogate may also be fused or combined in a formulation, or co-administered with an agent that enhances wnt activity, e.g. R-spondin 1, R-spondin 2, anti-sclerosin antibody, etc.

Linker.

The Fzd binding domain and the Lrp5/6 binding domain may be separated by a linker, e.g. a polypeptide linker, or a non-peptidic linker, etc. The amino acid linkers that join domains can play an important role in the structure and function of multi-domain proteins. There are numerous examples of proteins whose catalytic activity requires proper linker composition. In general, altering the length of linkers connecting domains has been shown to affect protein stability, folding rates and domain-domain orientation (see George and Hering (2003) Prot. Eng. 15:871-879). The length of the linker in the wnt surrogate, and therefore the spacing between the binding domains, can be used to modulate the signal strength of the wnt surrogate, and can be selected depending on the desired use of the wnt surrogate. The enforced distance between binding domains of a wnt surrogate can vary, but in certain embodiments may be less than about 100 angstroms, less than about 90 angstroms, less than about 80 angstroms, less than about 70 angstroms, less than about 60 angstroms, less than about 50 angstroms.

In some embodiments the linker is a rigid linker, in other embodiments the linker is a flexible linker. In some embodiments, the linker moiety is a peptide linker. In some embodiments, the peptide linker comprises 2 to 100 amino acids. In some embodiments, the peptide linker comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 but no greater than 100 amino acids. In some embodiments, the peptide linker is between 5 to 75, 5 to 50, 5 to 25, 5 to 20, 5 to 15, 5 to 10 or 5 to 9 amino acids in length. Exemplary linkers include linear peptides having at least two amino acid residues such as Gly-Gly, Gly-Ala-Gly, Gly-Pro-Ala, Gly-Gly-Gly-Gly-Ser. Suitable linear peptides include polyglycine, polyserine, polyproline, polyalanine and oligopeptides consisting of alanyl and/or serinyl and/or prolinyl and/or glycyl amino acid residues. In some embodiments, the peptide linker comprises the amino acid sequence selected from the group consisting of Gly$_9$, Glu$_9$, Ser$_9$, Gly$_5$-Cys-Pro$_2$-Cys, (Gly$_4$-Ser)$_3$, Ser-Cys-Val-Pro-Leu-Met-Arg-Cys-Gly-Gly-Cys-Cys-Asn, Pro-Ser-Cys-Val-Pro-Leu-Met-Arg-Cys-Gly-Gly-Cys-Cys-Asn, Gly-Asp-Leu-Ile-Tyr-Arg-Asn-Gln-Lys, and Gly$_9$-Pro-Ser-Cys-Val-Pro-Leu-Met-Arg-Cys-Gly-Gly-Cys-Cys-Asn. In one embodiment a linker comprises the amino acid sequence GSTSGSGKSSEGKG, or (GGGGS)n, where n is 1, 2, 3, 4, 5, etc.; however many such linkers are known and used in the art and may serve this purpose.

Wnt surrogates can be provided in single-chain form, which means that the binding domains are linked by peptide bonds through a linker peptide. In other embodiments, the binding domains are individual peptides and can be joined through a non-peptidic linker.

Chemical groups that find use in linking binding domains include carbamate; amide (amine plus carboxylic acid); ester (alcohol plus carboxylic acid), thioether (haloalkane plus sulfhydryl; maleimide plus sulfhydryl), Schiff's base (amine plus aldehyde), urea (amine plus isocyanate), thiourea (amine plus isothiocyanate), sulfonamide (amine plus sulfonyl chloride), disulfide; hyrodrazone, lipids, and the like, as known in the art.

The linkage between binding domains may comprise spacers, e.g. alkyl spacers, which may be linear or branched, usually linear, and may include one or more unsaturated bonds; usually having from one to about 300 carbon atoms; more usually from about one to 25 carbon atoms; and may be from about three to 12 carbon atoms. Spacers of this type may also comprise heteroatoms or functional groups, including amines, ethers, phosphodiesters, and the like. Specific structures of interest include: $(CH_2CH_2O)n$ where n is from 1 to about 12; $(CH_2CH_2NH)n$, where n is from 1 to about 12; $[(CH_2)n(C=O)NH(CH_2)_m]_z$, where n and m are from 1 to about 6, and z is from 1 to about 10; $[(CH_2)nOPO_3(CH_2)_m]_z$ where n and m are from 1 to about 6, and z is from 1 to about 10. Such linkers may include polyethylene glycol, which may be linear or branched.

The binding domains may be joined through a homo- or heterobifunctional linker having a group at one end capable of forming a stable linkage to the hydrophilic head group, and a group at the opposite end capable of forming a stable linkage to the targeting moiety. Illustrative entities include: azidobenzoyl hydrazide, N-[4-(p-azidosalicylamino)butyl]-3'-[2'-pyridyldithio]propionamide), bis-sulfosuccinimidyl suberate, dimethyladipimidate, disuccinimidyltartrate, N-γ-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl] aminobenzoate, glutaraldehyde, NHS-PEG-MAL; succinimidyl 4-[N-maleimidomethyl]cyclohexane-1-carboxylate; 3-(2-pyridyldithio)propionic acid N-hydroxysuccinimide ester (SPDP); N,N'-(1,3-phenylene) bismaleimide; N,N'-ethylene-bis-(iodoacetamide); or 4-(N-maleimidomethyl)-cyclohexane-1-carboxylic acid N-hydroxysuccinimide ester (SMCC); m-maleimidobenzoyl-N-hydroxysuccinimide ester (MBS), and succinimide 4-(p-maleimidophenyl) butyrate (SMPB), an extended chain analog of MBS. The succinimidyl group of these cross-linkers reacts with a primary amine, and the thiol-reactive maleimide forms a covalent bond with the thiol of a cysteine residue.

Other reagents useful for this purpose include: p,p'-difluoro-m,m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); disdiazobenzidine (which reacts primarily with tyrosine and histidine); O-benzotriazolyloxy tetramethuluronium hexafluorophosphate (HATU), dicyclohexyl carbodiimide, bromo-tris (pyrrolidino) phosphonium bromide (PyBroP); N,N-dimethylamino pyridine (DMAP); 4-pyrrolidino pyridine; N-hydroxy benzotriazole; and the like. Homobifunctional cross-linking reagents include bis-maleimidohexane ("BMH").

Antibody:

As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure.

The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation.

Any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, antibody sequence elements are humanized, primatized, chimeric, etc, as is known in the art.

Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgG, IgE and IgM, bi- or multi-specific antibodies (e.g., Zybodies®, etc), single chain Fvs, Fabs, Small Modular ImmunoPharmaceuticals ("SMIPs™"), single chain or Tandem diabodies (TendAb®), VHHs, Anticalins®, Nanobodies®, minibodies, BiTE®s, ankyrin repeat proteins or DARPINs®, Avimers®, a DART, a TCR-like antibody, Adnectins®, Affilins®, Trans-bodies®, Affibodies®, a TrimerX®, MicroProteins, Fynomers®, Centyrins®, and a KALBITOR®. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]

In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

The frizzled binding moiety of the surrogate may be an engineered protein that is selected for structural homology to the frizzled binding region of a wnt protein. Such proteins can be identified by screening a structure database for homologies. The initial protein thus identified, for example the microbial Bh1478 protein. The native protein is then engineered to provide amino acid substitutions that increase affinity, and may further be selected by affinity maturation for increased affinity and selectivity in binding to the desired frizzled protein. Non-limiting examples of frizzled binding moieties include the Fz27 and Fz27-B12 proteins illustrated in FIG. 1.

For example, without limitation the invention includes a polypeptide of FIG. 1 or an affinity matured variant thereof.

Figure 3:
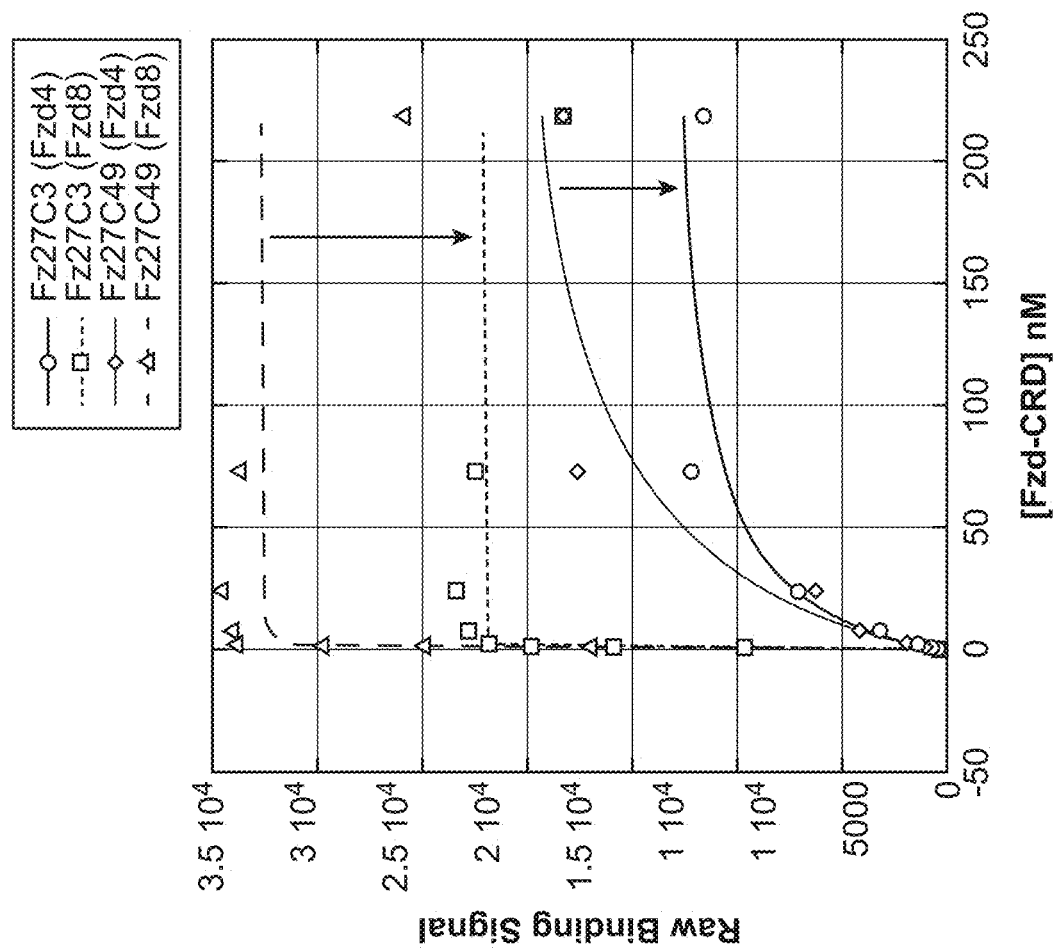
FIG. 3. Frizzled specificity of designed proteins. Approximate Kd's obtained from yeast surface titrations determined Fz27 variants to be highly specific for Fzd8-CRD compared to Fzd4-CRD by virtue of rational positive design for binding to Fzd8-CRD. The existing preference for Fzd8-CRD over Fzd4-CRD demonstrates an ability to design binders which can discriminate between Frizzled subtypes.

Affinity matured wnt peptide surrogates include, without limitation, those peptides mutated at selected positions and having an avidity enhanced $K_D$ of at least about $1\times10^{-7}$ M for Frizzled; at least about $1\times10^{-8}$ M; at least about $5\times10^{-9}$ M, or more. Examples of affinity matured wnt peptide surrogates include, without limitation. the B12 variant, as well as C3 and C49 variants depicted in FIG. 3.

Expression Construct:

In the present methods, a wnt surrogate, if a polypeptide, may be produced by recombinant methods. Amino acid sequence variants of are prepared by introducing appropriate nucleotide changes into the DNA coding sequence. Such variants represent insertions, substitutions, and/or specified deletions of, residues within or at one or both of the ends of the amino acid sequence. Any combination of insertion, substitution, and/or specified deletion is made to arrive at the final construct, provided that the final construct possesses the desired biological activity as defined herein. The amino acid changes also may alter post-translational processes of the polypeptide, such as changing the number or position of glycosylation sites, altering the membrane anchoring characteristics, and/or altering the cellular location by inserting, deleting, or otherwise affecting the leader sequence of a polypeptide.

The nucleic acid encoding the wnt surrogate can be inserted into a replicable vector for expression. Many such vectors are available. The vector components generally include, but are not limited to, one or more of the following: an origin of replication, one or more marker genes, an enhancer element, a promoter, and a transcription termination sequence.

Expression vectors will contain a promoter that is recognized by the host organism and is operably linked to the wnt surrogate coding sequence. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature.

Promoters suitable for use with prokaryotic hosts include the □-lactamase and lactose promoter systems, alkaline phosphatase, a tryptophan (trp) promoter system, and hybrid promoters such as the tac promoter. However, other known bacterial promoters are also suitable. Such nucleotide sequences have been published, thereby enabling a skilled worker operably to ligate them to a DNA coding sequence. Promoters for use in bacterial systems also will contain a Shine-Dalgarno (S.D.) sequence operably linked to the coding sequence.

Promoter sequences are known for eukaryotes. Examples of suitable promoting sequences for use with yeast hosts include the promoters for 3-phosphoglyceratekinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Transcription from vectors in mammalian host cells may be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, □-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence, but is preferably located at a site 5' from the promoter.

Expression vectors used in eukaryotic host cells (yeast, fungi, insect, plant, animal, human, or nucleated cells from other multicellular organisms) may also contain sequences necessary for the termination of transcription and for stabilizing the mRNA. Such sequences are commonly available from the 5' and, occasionally 3', untranslated regions of eukaryotic or viral DNAs or cDNAs.

Construction of suitable vectors containing one or more of the above-listed components employs standard techniques. Isolated plasmids or DNA fragments can be cleaved, tailored, and re-ligated in the form desired to generate the plasmids required. For analysis to confirm correct sequences in plasmids constructed, the ligation mixtures are used to transform host cells, and successful transformants selected by ampicillin or tetracycline resistance where appropriate. Plasmids from the transformants are prepared, analyzed by restriction endonuclease digestion, and/or sequenced.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. These examples are illustrative rather than limiting.

In addition to prokaryotes, eukaryotic microbes such as filamentous fungi or yeast are suitable expression hosts. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as *K. lactis, K. fragilis*, etc.; *Pichia pastoris; Candida; Neurospora crassa; Schwanniomyces* such as *Schwanniomyces occidentalis*; and filamentous fungi such as *Penicillium, Tolypocladium*, and *Aspergillus* hosts such as *A. nidulan*, and *A. niger*.

Plant cell cultures of cotton, corn, potato, soybean, *petunia*, tomato, and tobacco can be utilized as hosts. Typically, plant cells are transfected by incubation with certain strains of the bacterium *Agrobacterium tumefaciens*. During such incubation of the plant cell culture, the DNA coding sequence is transferred to the plant cell host such that it is transfected, and will, under appropriate conditions, express the DNA. In addition, regulatory and signal sequences compatible with plant cells are available, such as the nopaline synthase promoter and polyadenylation signal sequences.

Examples of useful mammalian host cell lines are mouse L cells (L-M[TK-], ATCC #CRL-2648), monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2).

Host cells are transfected with the above-described expression vectors for wnt surrogate production, and cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan.

Small Molecule Compositions.

Wnt surrogates of the invention also include organic molecules, preferably small organic compounds having a molecular weight of more than 50 and less than about 20,000 daltons. Useful surrogates are identified by, for example, a screening assay in which molecules are assayed for high affinity binding to one or both of an Fzd protein of interest, and Lrp5/6. A molecule can provide for a binding moiety that will be joined to another binding moiety, or joined to a binding domain as described above for polypeptide agents.

Candidate surrogates comprise functional groups necessary for structural interaction with proteins such as Fzd or Lrp5/6, particularly hydrogen bonding, and typically include at least an amine, carbonyl, hydroxyl or carboxyl group, preferably at least two of the functional chemical groups. The candidate surrogates often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate surrogates are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642, each of which is incorporated herein by reference.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Preliminary screens can be conducted by screening for compounds capable of binding to a Fzd or Lrp5/6 polypeptide. The binding assays usually involve contacting a Fzd or Lrp5/6 polypeptide with one or more test compounds and allowing sufficient time for the protein and test compounds to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in Neurotransmitter Receptor Binding (Yamamura, H. I., et al., eds.), pp. 61-89.

Certain screening methods involve screening for a compound that modulates wnt signaling activity. Such methods may involve conducting cell-based assays in which test compounds are contacted with one or more cells expressing Fzd and then detecting and an increase in expression of wnt-responsive genes, detecting nuclear localization of b-catenin, and the like.

The level of expression or activity can be compared to a baseline value. As indicated above, the baseline value can be a value for a control sample or a statistical value that is representative of expression levels for a control population. Expression levels can also be determined for cells that do not express a wnt receptor, as a negative control. Such cells generally are otherwise substantially genetically the same as the test cells. Various controls can be conducted to ensure that an observed activity is authentic including running parallel reactions with cells that lack the reporter construct or by not contacting a cell harboring the reporter construct with test compound. Compounds can also be further validated as described below.

Compounds that are initially identified by any of the foregoing screening methods can be further tested to validate the apparent activity. The basic format of such methods involves administering a lead compound identified during an initial screen to an animal or in a cell culture model, that serves as a model for humans. The animal models utilized in validation studies generally are mammals. Specific examples of suitable animals include, but are not limited to, primates, mice, and rats.

Active test agents identified by the screening methods described herein can serve as lead compounds for the synthesis of analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs for implementing these techniques are available. See, e.g., Rein et al., (1989) Computer-Assisted Modeling of Receptor-Ligand Interactions (Alan Liss, New York).

Pharmaceutical Compositions

For therapeutic applications, the wnt surrogate is administered to a mammal, preferably a human, in a physiologically acceptable dosage form, including those that may be administered to a human intravenously as a bolus or by continuous infusion over a period of time. Alternative routes of administration include topical, intramuscular, intraperitoneal, intra-cerobrospinal, subcutaneous, intra-articular, intrasynovial, intrathecal, oral, topical, or inhalation routes. The wnt surrogates also are suitably administered by intratumoral, peritumoral, intralesional, or perilesional routes or to the lymph, to exert local as well as systemic therapeutic effects.

Pharmaceutical compositions may also comprise combinations of the molecules of the invention with cells, including stem cells, progenitor cells, and the like. In some embodiments, the compositions comprise the molecules of the invention in combination with regenerative somatic stem cells, e.g. epithelial stem cells, neural stem cells, liver stem cells, hematopoietic stem cells, osteoblasts, muscle stem cells, mesenchymal stem cells, pancreatic stem cells, etc. In such combinations, cells can be pre-treated with a molecule of the invention prior to use, e.g. ex vivo treatment of cells with the wnt surrogate; cells can be administered concomitantly with a molecule of the invention in a separate or combined formulation; cells can be provided to an individual prior to treatment with a molecule of the invention, and the like.

The terms "stem cell" as used herein, refer to a cell that has the property of self-renewal and has the developmental potential to differentiate into multiple cell types. A stem cell is capable of proliferation and giving rise to more such stem cells while maintaining its developmental potential. Stem cells can divide asymmetrically, with one daughter cell retaining the developmental potential of the parent stem cell and the other daughter cell expressing some distinct other specific function, phenotype and/or developmental potential from the parent cell. The daughter cells themselves can be induced to proliferate and produce progeny that subsequently differentiate into one or more mature cell types, while also retaining one or more cells with parental developmental potential. A differentiated cell may derive from a multipotent cell, which itself is derived from a multipotent cell, and so on. While each of these multipotent cells may be considered stem cells, the range of cell types each such stem cell can give rise to, i.e., their developmental potential, can vary considerably. Alternatively, some of the stem cells in a population can divide symmetrically into two stem cells, known as stochastic differentiation, thus maintaining some stem cells in the population as a whole, while other cells in the population give rise to differentiated progeny only. Accordingly, the term "stem cell" refers to any subset of cells that have the developmental potential, under particular circumstances, to differentiate to a more specialized or differentiated phenotype, and which retain the capacity, under certain circumstances, to proliferate without substantially differentiating.

The term "somatic stem cell" is used herein to refer to any pluripotent or multipotent stem cell derived from non-embryonic tissue, including fetal, juvenile, and adult tissue. Natural somatic stem cells have been isolated from a wide variety of adult tissues including blood, bone marrow, brain, olfactory epithelium, skin, pancreas, skeletal muscle, and cardiac muscle. The term "progenitor cell" is used herein to refer to cells that are at an earlier stage along a developmental pathway or progression, relative to a cell which it can give rise to by differentiation. Often, progenitor cells have significant or very high proliferative potential. Progenitor cells can give rise to multiple distinct differentiated cell types, or to a single differentiated cell type, depending on the developmental pathway and on the environment in which the cells develop and differentiate.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$ Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The effective amount of a therapeutic composition to be given to a particular patient will depend on a variety of factors, several of which will be different from patient to patient. A formulation may be provided, for example, in a unit dose. A competent clinician will be able to determine an effective amount of a therapeutic agent to administer to a patient. Dosage of the surrogate will depend on the treatment, route of administration, the nature of the therapeutics, sensitivity of the disease to the therapeutics, etc. Utilizing $LD_{50}$ animal data, and other information available, a clinician can determine the maximum safe dose for an individual, depending on the route of administration. Compositions which are rapidly cleared from the body may be administered at higher doses, or in repeated doses, in order to maintain a therapeutic concentration. Utilizing ordinary skill, the competent clinician will be able to optimize the dosage of a particular therapeutic or imaging composition in the course of routine clinical trials. Typically the dosage will be 0.001 to 100 milligrams of agent per kilogram subject body weight.

The compositions can be administered to the subject in a series of more than one administration. For therapeutic compositions, regular periodic administration (e.g., every 2-3 days) will sometimes be required, or may be desirable to reduce toxicity. For therapeutic compositions which will be utilized in repeated-dose regimens, moieties which do not provoke immune responses are preferred.

In another embodiment of the invention, an article of manufacture containing materials useful for the treatment of the conditions described herein is provided. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). The active agent in the composition is the wnt surrogate. The label on, or associated with, the container indicates that the composition is used for treating the condition of choice. Further container(s) may be provided with the article of manufacture which may hold, for example, a pharmaceutically-acceptable buffer, such as phosphate-buffered saline, Ringer's solution or dextrose solution. The article of manufacture may further include other materials desirable from a commercial and user standpoint, including other buffers, diluents, filters, needles, syringes, and package inserts with instructions for use.

As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, stabilizes one or more characteristics of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment.

For example, in some embodiments, term "therapeutically effective amount", refers to an amount which, when administered to an individual in need thereof in the context of inventive therapy, will block, stabilize, attenuate, or reverse a disease process occurring in said individual.

Methods of Use

The wnt surrogates are useful for both prophylactic and therapeutic purposes. Thus, as used herein, the term "treating" is used to refer to both prevention of disease, and treatment of a pre-existing condition. In certain instances, prevention indicates inhibiting or delaying the onset of a disease or condition, in a patient identified as being at risk of developing the disease or condition. The treatment of ongoing disease, to stabilize or improve the clinical symptoms of the patient, is a particularly important benefit provided by the present invention. Such treatment is desirably performed prior to loss of function in the affected tissues; consequently, the prophylactic therapeutic benefits provided by the invention are also important. Evidence of therapeutic effect may be any diminution in the severity of disease. The therapeutic effect can be measured in terms of clinical outcome or can be determined by immunological or biochemical tests. Patients for treatment may be mammals, e.g. primates, including humans, may be laboratory animals, e.g. rabbits, rats, mice, etc., particularly for evaluation of therapies, horses, dogs, cats, farm animals, etc.

The dosage of the therapeutic formulation, e.g., pharmaceutical composition, will vary widely, depending upon the nature of the condition, the frequency of administration, the manner of administration, the clearance of the agent from the host, and the like. In particular embodiments, the initial dose can be larger, followed by smaller maintenance doses. In certain embodiments, the dose can be administered as infrequently as weekly or biweekly, or more often fractionated into smaller doses and administered daily, semi-weekly, or otherwise as needed to maintain an effective dosage level.

In some embodiments of the invention, administration of the composition or formulation comprising the wnt surrogate is performed by local administration. Local administration, as used herein, may refer to topical administration, but also refers to injection or other introduction into the body at a site of treatment. Examples of such administration include intramuscular injection, subcutaneous injection, intraperitoneal injection, and the like. In other embodiments, the composition or formulation comprising the wnt surrogate is administered systemically, e.g., orally or intravenously. In one embodiment, the composition of formulation comprising the wnt surrogate is administered by infusion, e.g., continuous infusion over a period of time, e.g., 10 min, 20 min, 3 min, one hour, two hours, three hours, four hours, or greater.

In some embodiments of the invention, the compositions or formulations are administered on a short term basis, for example a single administration, or a series of administrations performed over, e.g. 1, 2, 3 or more days, up to 1 or 2 weeks, in order to obtain a rapid, significant increase in activity. The size of the dose administered must be determined by a physician and will depend on a number of factors, such as the nature and gravity of the disease, the age and state of health of the patient and the patient's tolerance to the drug itself.

In certain methods of the present invention, an effective amount of a composition comprising a wnt surrogate is provided to cells, e.g. by contacting the cell with an effective amount of that composition to achieve a desired effect, e.g. to enhance Wnt signaling, proliferation, etc. In particular embodiments, the contacting occurs in vitro, ex vivo or in vivo. In particular embodiments, the cells are derived from or present within a subject in need or increased Wnt signaling.

In some methods of the invention, an effective amount of the subject composition is provided to enhance Wnt signaling in a cell. Biochemically speaking, an effective amount or effective dose of a Wnt surrogate is an amount to increase Wnt signaling in a cell by at least 30%, at least 40%, at least 50%, at least 60%, at least 70%, at least 80%, at least 90%, at least 95%, or by 100% relative to the signaling in the absence of the wnt surrogate. The amount of modulation of a cell's activity can be determined by a number of ways known to one of ordinary skill in the art of wnt biology.

In a clinical sense, an effective dose of a wnt surrogate composition is the dose that, when administered to a subject for a suitable period of time, e.g., at least about one week, and maybe about two weeks, or more, up to a period of about 4 weeks, 8 weeks, or longer, will evidence an alteration in the symptoms associated with lack of wnt signaling. In some embodiments, an effective dose may not only slow or halt the progression of the disease condition but may also induce the reversal of the condition. It will be understood by those of skill in the art that an initial dose may be administered for such periods of time, followed by maintenance doses, which, in some cases, will be at a reduced dosage.

The calculation of the effective amount or effective dose of wnt surrogate composition to be administered is within the skill of one of ordinary skill in the art, and will be routine to those persons skilled in the art. Needless to say, the final amount to be administered will be dependent upon the route of administration and upon the nature of the disorder or condition that is to be treated.

Cells suitable for use in the subject methods are cells that comprise one or more Fzd receptors. The cells to be contacted may be in vitro, that is, in culture, or they may be in vivo, that is, in a subject. Cells may be from/in any organism, but are preferably from a mammal, including humans, domestic and farm animals, and zoo, laboratory or pet animals, such as dogs, cats, cattle, horses, sheep, pigs, goats, rabbits, rats, mice, frogs, zebrafish, fruit fly, worm, etc. Preferably, the mammal is human. Cells may be from any tissue. Cells may be frozen, or they may be fresh. They may be primary cells, or they may be cell lines. Often cells are primary cells used in vivo, or treated ex vivo prior to introduction into a recipient.

Cells in vitro may be contacted with a composition comprising a wnt surrogate by any of a number of well-known methods in the art. For example, the composition may be provided to the cells in the media in which the subject cells are being cultured. Nucleic acids encoding the wnt surrogate may be provided to the subject cells or to cells co-cultured with the subject cells on vectors under conditions that are well known in the art for promoting their uptake, for example electroporation, calcium chloride transfection, and lipofection. Alternatively, nucleic acids encoding the wnt surrogate may be provided to the subject cells or to cells cocultured with the subject cells via a virus, i.e. the cells are contacted with viral particles comprising nucleic acids encoding the wnt peptide surrogate polypeptide. Retroviruses, for example, lentiviruses, are particularly suitable to the method of the invention, as they can be used to transfect non-dividing cells (see, for example, Uchida et al. (1998) P.N.A.S. 95(20):11939-44). Commonly used retroviral vectors are "defective", i.e. unable to produce viral proteins required for productive infection. Rather, replication of the vector requires growth in a packaging cell line.

Likewise, cells in vivo may be contacted with the subject wnt surrogate compositions by any of a number of well-known methods in the art for the administration of peptides, small molecules, or nucleic acids to a subject. The wnt surrogate composition can be incorporated into a variety of formulations or pharmaceutical compositions, which in some embodiments will be formulated in the absence of detergents, liposomes, etc., as have been described for the formulation of full-length Wnt proteins.

WNT signaling is required for the healing of almost every tissue in the human body. For example, WNTs have been shown to activate adult, tissue-resident stem cells. These stem cells self-renew and divide, and in doing so give rise to progeny cells that mature into the tissue of interest. The molecules of the present invention provide WNT activity in a pharmacologically acceptable format, which can be tailored to the Fzd receptors present in the tissue of interest.

In some embodiments, the compounds of the invention are administered for use in treating diseased or damaged tissue, for use in tissue regeneration and for use in cell growth and proliferation, and/or for use in tissue engineering. In particular, the present invention provides a wnt surrogate, or a composition comprising one or more surrogates according to the invention for use in treating tissue loss or damage due to aging, trauma, infection, or other pathological conditions.

Conditions of interest for treatment with the compositions of the invention include, without limitation, a number of conditions in which regenerative cell growth is desired. Such conditions can include, for example, enhanced bone growth or regeneration, e.g. on bone regeneration, bone grafts, healing of bone fractures, etc.; treatment of alopecia; enhanced regeneration of sensory organs, e.g. treatment of hearing loss, treatment of macular degeneration, etc.; tooth growth, tooth regeneration, treatment of stroke, traumatic brain injury, Alzheimer's disease, multiple sclerosis and other conditions affecting the blood brain barrier; treatment of oral mucositis, conditions where enhanced epidermal regeneration is desired, e.g. epidermal wound healing, treatment of diabetic foot ulcers, etc., enhanced growth of hematopoietic cells, e.g. enhancement of hematopoietic stem cell transplants from bone marrow, mobilized peripheral blood, treatment of immunodeficiencies, etc.; enhanced regeneration of liver cells, e.g. liver regeneration, treatment of cirrhosis, enhancement of liver transplantations, and the like.

Conditions in which enhanced bone growth is desired may include, without limitation, fractures, grafts, ingrowth around prosthetic devices, and the like. WNT proteins are critical regulators of bone turnover, and abundant scientific data supports a role for these proteins in promoting bone regeneration. In some embodiments, bone marrow cells are exposed to molecules of the invention, such that stem cells within that marrow become activated. These activated cells can remain in situ for the benefit of the individual, or can be used in bone grafting procedures.

In some embodiments, bone regeneration is enhanced by contacting a responsive cell population, e.g. bone marrow, bone progenitor cells, bone stem cells, etc. with an effective dose of a molecule of the invention. In some such embodiments, the contacting is performed in vivo. In other such embodiments, the contacting is performed ex vivo. The molecule may be localized to the site of action, e.g. by loading onto a matrix, which is optionally biodegradable, and optionally provides for a sustained release of the active agent. Matrix carriers include, without limitation, absorbable collagen sponges, ceramics, hydrogels, bone cements, and the like.

Compositions comprising one or more of the molecules of the invention can be used in the in vitro generation of skeletal tissue, such as from skeletogenic stem cells, as well as the in vivo treatment of skeletal tissue deficiencies. The subject compounds may be used to regulate the rate of chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions. For example, the compositions of the present invention can be used as part of a regimen for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a laxation of a joint by a torn ligament, malignment of joints, bone fracture, or by hereditary disease.

The compositions of the invention also find use in regeneration of tissues in the eye. Age-related macular degeneration (AMD) is characterized by progressively decreased central vision and visual acuity and remains a leading cause of vision loss and blindness in aged Americans. Currently, the standard of care for AMD is intravitreal vascular endothelial growth factor (VEGF) inhibitors. AMD is a multi-factorial disease involving numerous pathogenic factors, such as VEGF, platelet-derived growth factor (PDGF), intercellular adhesion molecule-1 (ICAM-1), tumor necrosis factor-alpha (TNF-α), cyclooxygenase-2 (Cox-2), connective tissue growth factor (CTGF), and fibronectin (FN), that contribute to angiogenesis, inflammation, fibrosis and oxidative stress in AMD. Compositions of the present invention can be used, for example, in an infusion; in a matrix or other depot system; or other topical application to the eye for treatment of macular degeneration.

In other embodiments, the compositions of the invention are used in the regeneration of retinal tissue. In the adult mammalian retina, Müller glia dedifferentiate and produce retinal cells, including photoreceptors, for example after neurotoxic injury in vivo. However, the number of newly generated retinal neurons is very limited. However wnt signaling can promote proliferation of Müller glia-derived retinal progenitors and neural regeneration after damage or during degeneration. Compositions of the present invention can be used, for example, in an infusion; in a matrix or other depot system; or other topical application to the eye for enhancement of retinal regeneration.

Other sensory organs, such as the cells involved in hearing loss, also benefit from the compositions of the invention. In the inner ear, the auditory organ houses mechanosensitive hair cells required for translating sound vibration to electric impulses. The vestibular organs, comprised of the semicircular canals (SSCs), the utricle, and the saccule, also contain sensory hair cells in order to detect head position and motion. Both auditory and vestibular signals are in turn relayed centrally via the spiral and vestibular ganglion neurons, allowing for sound and balance perception. Numerous studies have characterized the multiple roles of the Wnt signaling during cochlear development and in promoting hair cell regeneration. Mature mammalian auditory and vestibular organs do not spontaneously mount a proliferative response after hair cell degeneration. However, active Wnt/β-catenin signaling can promote proliferation of hair cells, where Lgr5-positive supporting cells can behave as hair cell progenitors. Lgr5-positive supporting cells can mitotically regenerate hair cells, where Wnt signaling augments both the mitotic response and the extent of hair cell regeneration. Wnt signaling can also induce ectopic hair cell formation. Compositions of the present invention can be used, for example, in an infusion; in a matrix or other depot system; or other topical application to the ear for enhancement of auditory regeneration.

Periodontal diseases are a leading cause of tooth loss and are linked to multiple systemic conditions. Reconstruction of the support and function of affected tooth-supporting tissues represents an important therapeutic endpoint for periodontal regenerative medicine. An improved understanding of periodontal biology coupled with current advances in scaffolding matrices provides treatments that provide the compositions of the invention, optionally in combination with delivery of regenerative cells for the predictable tissue regeneration of supporting alveolar bone, periodontal ligament, and cementum. In some embodiments, tooth or underlying bone regeneration is enhanced by contacting a responsive cell population with an effective dose of a molecule of the invention. In some such embodiments, the contacting is performed in vivo. In other such embodiments, the contacting is performed ex vivo, with subsequent implantation of the activated stem or progenitor cells. The molecule may be localized to the site of action, e.g. by loading onto a matrix, which is optionally biodegradable, and optionally provides for a sustained release of the active agent. Matrix carriers include, without limitation, absorbable collagen sponges, ceramics, hydrogels, bone cements, and the like.

Hair loss is a common problem with multiple causes that range from hormone sensitivity to autoimmunity. Androgenetic alopecia, often called male pattern baldness, is the most common form of hair loss in men, which affects as many as 50% of men as they age. In androgenetic alopecia, hair loss is caused by a sensitivity of hair follicles in the top of the scalp to the androgen 5α-dihydrotestosterone (DHT). DHT causes those follicles to undergo a progressive miniaturization to the point where they no longer produce a clinically apparent hair shaft. The cells affected by DHT are the dermal papilla cells, which cease growing and lose their ability to direct hair growth. Epidermal Wnt signaling is critical for adult hair follicle regeneration. In some embodiments, hair follicle regeneration is enhanced by contacting a responsive cell population with an effective dose of a molecule of the invention. In some such embodiments, the contacting is performed in vivo. In other such embodiments, the contacting is performed ex vivo, with subsequent implantation of the activated stem or progenitor cells, e.g. follicular cells. The molecule may be localized to the site of action, e.g. topical lotions, gels, creams and the like.

Various epidermal conditions benefit from treatment with the compounds of the invention. Mucositis occurs when there is a break down of the rapidly divided epithelial cells lining the gastro-intestinal tract, leaving the mucosal tissue open to ulceration and infection. Mucosal tissue, also known as mucosa or the mucous membrane, lines all body passages that communicate with the air, such as the respiratory and alimentary tracts, and have cells and associated glands that secrete mucus. The part of this lining that covers the mouth, called the oral mucosa, is one of the most sensitive parts of the body and is particularly vulnerable to chemotherapy and radiation. The oral cavity is the most common location for mucositis. Oral mucositis is probably the most common, debilitating complication of cancer treatments, particularly chemotherapy and radiation. It can lead to several problems, including pain, nutritional problems as a result of inability to eat, and increased risk of infection due to open sores in the mucosa. It has a significant effect on the patient's quality of life and can be dose-limiting (i.e., requiring a reduction in subsequent chemotherapy doses). Other epidermal conditions include epidermal wound healing, diabetic foot ulcers, and the like. Molecules of the invention can find use in such conditions, where regenerative cells are contacted with compounds of the invention. Contacting can be, for example, topical, including intradermal, subdermal, in a gel, lotion, cream etc. applied at targeted site, etc.

The liver has a capacity for regeneration, which can be enhanced by wnt signaling. Adult hepatic progenitor (oval) cells are facultative stem cells in liver. Active Wnt/β-catenin signaling occurs preferentially within the oval cell population, and wnt signaling promotes expansion of the oval cell population in a regenerated liver. Methods for regeneration of liver tissue benefits from administration of the compounds of the invention, which can be systemic or localized, e.g. by injection into the liver tissue, by injection into veins leading into the liver, by implantation of a sustained release formulation, and the like. Liver damage can be associated with infection, alcohol abuse, etc.

Stroke, traumatic brain injury, Alzheimer's, multiple sclerosis and other conditions affecting the blood-brain barrier. Angiogenesis is critical to ensure the supply of oxygen and nutrients to many tissues throughout the body, and is especially important for the CNS as the neural tissue is extremely sensitive to hypoxia and ischemia. The blood vessels in the brain form a specialized structure, termed the blood brain barrier (BBB), which limits the flow of molecules and ions from the blood to the brain. This BBB is critical to maintain brain homeostasis and protect the CNS from toxins and pathogens. CNS endothelial cells which form the BBB differ from endothelial cells in non-neural tissue, in that they are highly polarized cells held together by tight junctions that limit the paracellular flow of molecules and ions. In addition, CNS endothelial cells also express specific transporters, both to provide selective transport of essential nutrients across the BBB into the brain and to efflux potential toxins from the brain. Wnt signaling specifically regulates CNS vessel formation and/or function. Conditions in which the BBB is compromised can benefit from administration of the compounds of the invention, e.g. by direct injection, intrathecal administration, implantation of sustained release formulations, and the like.

The patient may be any animal (e.g., a mammal), including, but not limited to, humans, non-human primates, rodents, and the like. Typically, the patient is human. The methods of treatment and medical uses of the surrogates of the invention or compounds or compositions comprising surrogates of the invention promote tissue regeneration. The term "tissue" refers to part of an organism consisting of a cell or an aggregate of cells, optionally having a similar structure, function and/or origin. Examples of tissues include but are not limited to: epithelial tissues, such as skin tissue, stomach lining, pancreatic lining, liver; connective tissues, such as inner layers of skin, tendons, ligaments, cartilage, bone, fat, hair, blood; muscle tissues; and nerve tissues, such as glial cells and neurons. The loss or damage can be anything which causes the cell number to diminish. For example, an accident, an autoimmune disorder, a therapeutic side-effect or a disease state could constitute trauma. Specific examples of conditions which may cause cell number to diminish include, but are not limited to: radiation/chemotherapy, mucositis, IBD, short bowel syndrome, hereditary bowel disorders, celiac disease, metabolic diseases, hereditary syndromes, (viral) infections (hepB/C), toxic states, alcoholic liver, fatty liver, cirrhosis, infections, pernicious anemia, ulceration, diabetes, diabetic foot ulcers (e.g., refractory diabetic foot ulcers), destruction of islet cells, loss of bone mass (osteoporosis), loss of functional skin, loss of hair, loss of functional lung tissue, loss of kidney tissue (for instance acute tubulus necrosis), loss of sensory cells in the inner ear. Tissue regeneration increases the cell number within the tissue and preferably enables connections between cells of the tissue to be re-established, and more preferably the functionality of the tissue to be regained.

Other conditions that may be treated with the surrogates or compositions comprising one or more surrogates of the invention include but are not limited to: joint disorders, osteoporosis and related bone diseases, baldness, graft-versus-host disease.

Surrogates or compositions comprising one or more surrogates of the invention, e.g., surrogates that bind and activate LRP6, may also be used for wound healing and generation of smooth muscle tissues in many organs (e.g. airways, large arteries, uterus).

In some embodiments, the invention provides methods of treatment and medical uses, as described previously, wherein two or more surrogates of the invention or compounds or compositions comprising surrogates of the invention, are administered to an animal or patient simultaneously, sequentially, or separately. The surrogate(s) may also be administered simultaneously, sequentially, or separately with an agent that enhances wnt signaling, e.g. R-spondin1, R-spondin2, anti-sclerostin, etc.

In some embodiments, the invention provides methods of treatment and medical uses, as described previously, wherein one or more surrogates of the invention or compounds or compositions comprising surrogates of the invention, is administered to an animal or patient in combination with one or more further compound or drug, and wherein said surrogates of the invention or compounds or compositions comprising surrogates of the invention and said further compound or drug are administered simultaneously, sequentially, or separately.

The surrogates of the invention also have widespread applications in non-therapeutic methods, for example in vitro research methods.

The invention provides a method for tissue regeneration of damaged tissue, such as the tissues discussed in the section of medical uses above, comprising administering a surrogate of the invention. The surrogate may be administered directly to the cells in vivo, administered to the patient orally, intravenously, or by other methods known in the art, or administered to ex vivo cells. In some embodiments where the surrogate of the invention is administered to ex vivo cells, these cells may be transplanted into a patient before, after or during administration of the agonist of the invention.

The invention also provides a method for enhancing the proliferation of cells comprising supplying the cells with a surrogate of the invention.

These methods may be carried out in vivo, ex vivo or in vitro.

Wnt signaling is a key component of stem cell culture. For example, the stem cell culture media as described in WO2010/090513, WO2012/014076, Sato et al., 2011 (GASTROENTEROLOGY 2011; 141:1762-1772) and Sato et al., 2009 (Nature 459, 262-5). The surrogates of the invention are suitable alternatives to Rspondin for use in these stem cell culture media, or may be combined with Rspondin.

Accordingly, in one embodiment, the invention provides a method for enhancing the proliferation of stem cells comprising supplying stem cells with surrogates of the invention. In one embodiment, the invention provides a cell culture medium comprising one or more surrogates of the invention. In some embodiments, the cell culture medium may be any cell culture medium already known in the art that normally comprises Wnt or Rspondin, but wherein the Wnt or Rspondin is replaced (wholly or partially) or supplemented by surrogates of the invention. For example, the culture medium may be as described in as described in WO2010/090513, WO2012/014076, Sato et al., 2011 (GASTROENTEROLOGY 2011; 141:1762-1772) and Sato et al., 2009 (Nature 459, 262-5), which are hereby incorporated by reference in their entirety.

Stem cell culture media often comprise additional growth factors. This method may thus additionally comprise supplying the stem cells with a growth factor. Growth factors commonly used in cell culture medium include epidermal growth factor (EGF, (Peprotech), Transforming Growth Factor-alpha (TGF-alpha, Peprotech), basic Fibroblast Growth Factor (bFGF, Peprotech), brain-derived neurotrophic factor (BDNF, R&D Systems), Human Growth Factor (HGF) and Keratinocyte Growth Factor (KGF, Peprotech, also known as FGF7). EGF is a potent mitogenic factor for a variety of cultured ectodermal and mesodermal cells and has a profound effect on the differentiation of specific cells in vivo and in vitro and of some fibroblasts in cell culture. The EGF precursor exists as a membrane-bound molecule which is proteolytically cleaved to generate the 53-amino acid peptide hormone that stimulates cells. EGF or other mitogenic growth factors may thus be supplied to the stem cells. During culturing of stem cells, the mitogenic growth factor may be added to the culture medium every second day, while the culture medium is refreshed preferably every fourth day. In general, a mitogenic factor is selected from the groups consisting of: i) EGF, TGF-.alpha. and KGF, ii) EGF, TGF-.alpha. and FGF7; iii) EGF, TGF-.alpha. and FGF; iv)

EGF and KGF; v) EGF and FGF7; vi) EGF and a FGF; vii) TGF-α and KGF; viii) TGF-.alpha. and FGF7; ix) or from TGF α and a FGF.

These methods of enhancing proliferation of stem cells can be used to grow new organoids and tissues from stem cells, as for example described in WO2010/090513 WO2012/014076, Sato et al., 2011 (GASTROENTEROLOGY 2011; 141:1762-1772) and Sato et al., 2009 (Nature 459, 262-5).

A number of clinically relevant conditions are characterized by an inability to regenerate tissues, where upregulation of wnt signaling is desirable.

In some embodiments the wnt surrogate is used to enhance stem cell regeneration. Stem cells of interest include muscle satellite cells; hematopoietic stem cells and progenitor cells derived therefrom (U.S. Pat. No. 5,061,620); neural stem cells (see Morrison et al. (1999) Cell 96: 737-749); embryonic stem cells; mesenchymal stem cells; mesodermal stem cells; liver stem cells, etc.

The wnt surrogates find use in enhancing bone healing. In many clinical situations, the bone healing condition are less ideal due to decreased activity of bone forming cells, e.g. within aged people, following injury, in osteogenesis imperfecta, etc. A variety of bone and cartilage disorders affect aged individuals. Such tissues are normally regenerated by mesenchymal stem cells. Included in such conditions is osteoarthritis. Osteoarthritis occurs in the joints of the body as an expression of "wear-and-tear". Thus athletes or overweight individuals develop osteoarthritis in large joints (knees, shoulders, hips) due to loss or damage of cartilage. This hard, smooth cushion that covers the bony joint surfaces is composed primarily of collagen, the structural protein in the body, which forms a mesh to give support and flexibility to the joint. When cartilage is damaged and lost, the bone surfaces undergo abnormal changes. There is some inflammation, but not as much as is seen with other types of arthritis. Nevertheless, osteoarthritis is responsible for considerable pain and disability in older persons.

In methods of accelerating bone repair, a pharmaceutical wnt composition of the present invention is administered to a patient suffering from damage to a bone, e.g. following an injury. The formulation is preferably administered at or near the site of injury, following damage requiring bone regeneration. The wnt formulation is preferably administered for a short period of time, and in a dose that is effective to increase the number of bone progenitor cells present at the site of injury. In some embodiments the wnt is administered within about two days, usually within about 1 day of injury, and is provided for not more than about two weeks, not more than about one week, not more than about 5 days, not more than about 3 days, etc.

In an alternative method, patient suffering from damage to a bone is provided with a composition comprising bone marrow cells, e.g. a composition including mesenchymal stem cells, bone marrow cells capable of differentiating into osteoblasts; etc. The bone marrow cells may be treated ex vivo with a pharmaceutical composition comprising a wnt protein or proteins in a dose sufficient to enhance regeneration; or the cell composition may be administered to a patient in conjunction with a wnt formulation of the invention.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Based on the crystal structure of Wnt bound to Frizzled-CRD, an in silico design was used to develop a new protein that would mimic how Wnt binds to Fz-CRD using a lipid group. Computational methods identified uncharacterized protein Bh1478 from *Bacillus halodurans*, as a candidate scaffold for engineering. The protein, identified in FIG. 1 as 2QUP, has a published structure and the amino acid sequence:

```
                                      (SEQ ID NO: 39)
MDVQRVGKAGLHRVDSKKQQTAAGVSFSEVMGKQRDEKAYERLQALMS

KIDDQGKLLSETRTIEELRKYKELVKEFVGDAVELGLRLEERRGFNRR

GRTKIYKIVKEVDRKLLDLTDAVLAKEKKGLDILNMVGEIKGLLINIY

A
```

The scaffold sequence does not bind to frizzled (Fz8-CRD) but after selection of a library with mutagenized residues for increased affinity in a yeast system, the proteins Fz27 and Fz27-B12 (shown in FIG. 1); were developed. These proteins contain amino acid substitutions at positions 169, 170, 171, 173, 174, 176, 177, 178 and 179 relative to the scaffold. The sequences of the engineered proteins are shown in FIG. 1:

```
Fz27:
                                      (SEQ ID NO: 17)
Mgvsfsevmgkqkdeqareqlkegmkkieeqgkklsetrtqeelqkya aavaafaaaagflgknleerrgfnrrgkeeigkisgevykklldlkka vrakekkgldilnmvgeikglleriya Fz27-B12
                                      (SEQ ID NO: 18)
mgvsfsevmgkqkdeqareqlkegmikieeqgkklsetrtqeelqkyv aavatfalqagflgpnleerrgfnrrgkeeigkisgevylklldlkka vrakekkgldilnmvgeikgtlervya
```

FIG. 1 illustrates the structure and binding properties of the wnt surrogate proteins, and the frizzled binding domains. The interface, core and structural residues that contribute to affinity maturation are shown in FIG. 1.

Figure 2:
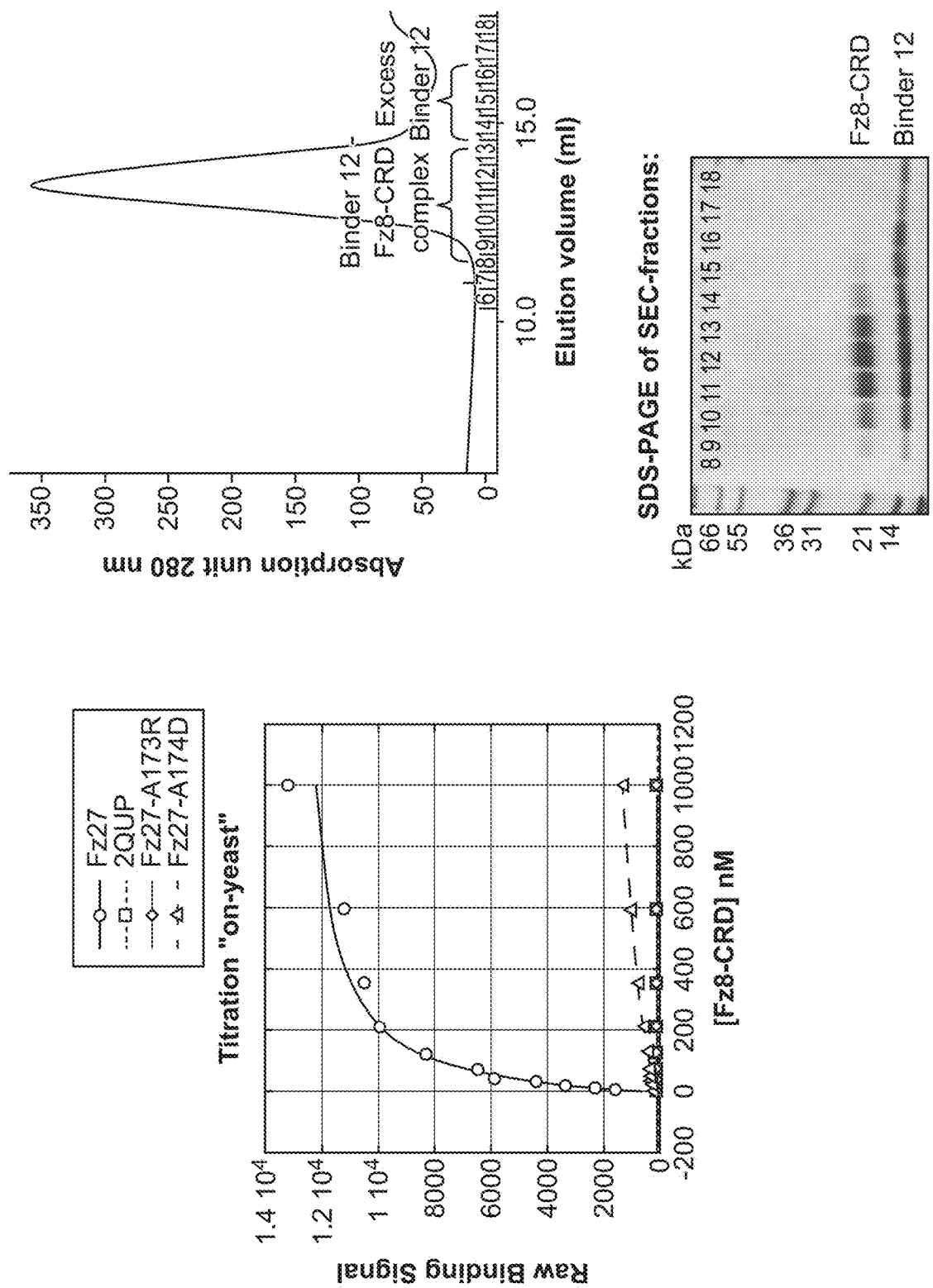
FIG. 2. Fz27-B12 binds to Fz8 with high affinity. Fz27 was expressed in a construct enabling binding to be confirmed via yeast surface display using fluorescence-conjugated Fz8-CRD. Knockout mutations (A173R/A174D) eliminated or significantly abrogated binding, indicating that the protein bound via the designed binding mode. The wild-type scaffold used to generate the design (2QUP) does not bind, indicating that binding activity is due to rational engineering.

As shown in FIG. 2, the engineered protein binds to Fz8 with a high affinity, while the parent scaffold protein does not bind. Amino acid substitutions A173R and A174D (corresponding to residues 53 and 54 in the sequence shown above) abrogate binding, as shown in FIG. 2A, indicating that the protein bound via the designed binding mode. Fz27 was expressed in a construct enabling binding to be confirmed via yeast surface display using fluorescence-conjugated Fz8-CRD. The wild-type scaffold used to generate the design (2QUP) does not bind, indicating that binding activity is due to rational engineering.

Approximate Kd's obtained from yeast surface titrations determined Fz27 variants to be highly specific for Fzd8-

CRD compared to Fzd4-CRD by virtue of rational positive design for binding to Fzd8-CRD. The existing preference for Fzd8-CRD over Fzd4-CRD demonstrates an ability to design binders which can discriminate even between Frizzled subtypes whose sequences are highly similar, shown in FIG. 3.

Figure 4:
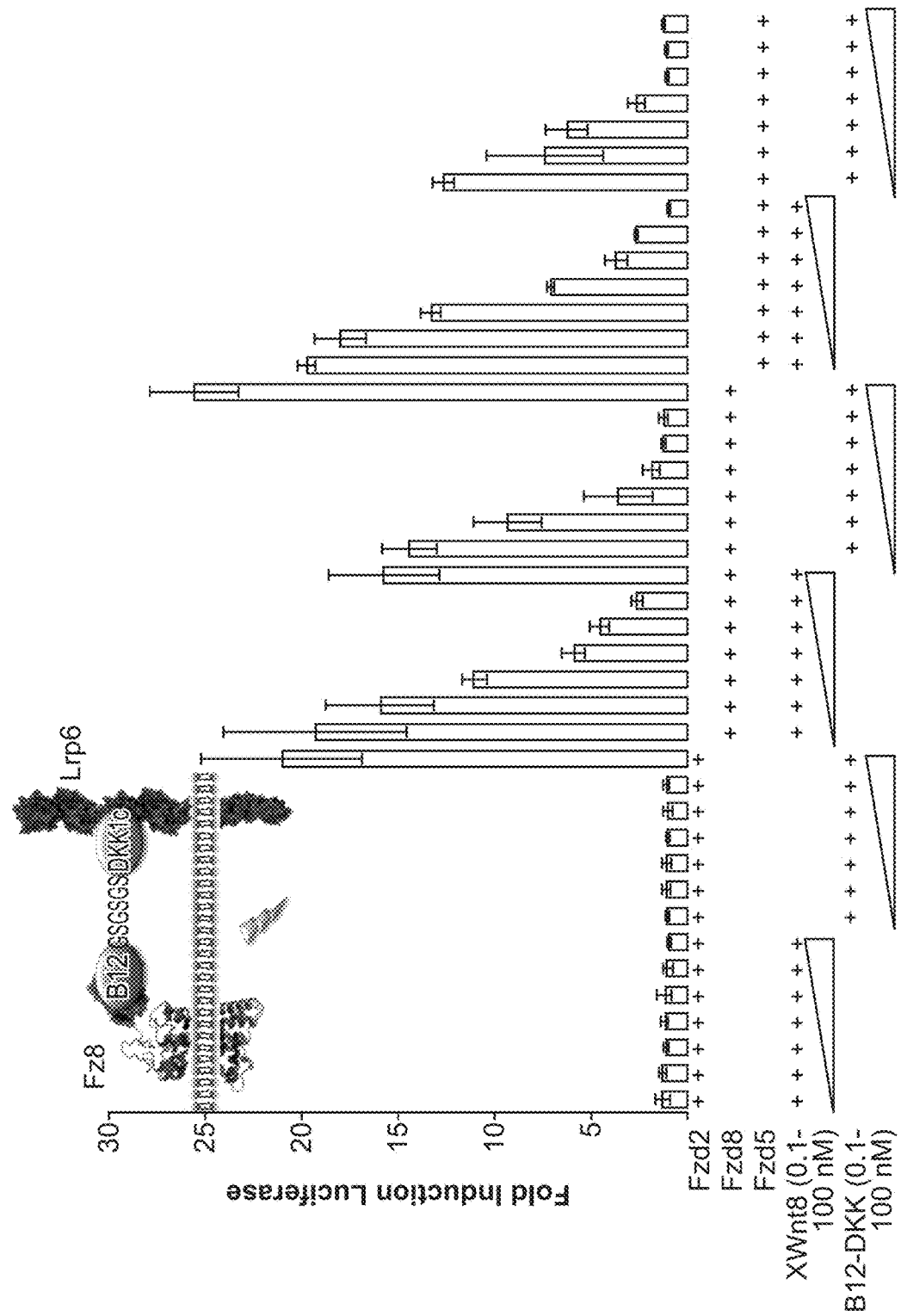
FIG. 4. B12-DKK1c recapitulates XWnt8 activity to activate the expression of the Wnt-signaling dependent luciferase reporter in mouse L-cell cells over-expressing Fzd5 and Fzd8. Mouse L-cells, stably transfected with the SuperTopFlash reporter, a firefly luciferase reporter with upstream concatamers of 7 TCF/LEF binding sites, and transiently transfected with Fzd5, Fzd8 or mock plasmid, were treated for 16-20 hrs with XWnt8 or B12-DKK1c. After, cells were lysed and the Wnt-signaling dependent expression of the firefly luciferase was detected with the Dual-Luciferase reporter system.

The engineered protein Fz27-B12 was joined through the short polypeptide linker, GSGSGS (SEQ ID NO: 19) to the Lrp6 binding domain of DKK1C, to create a wnt surrogate. Shown in FIG. 4, the surrogate protein recapitulates XWnt8 activity to activate Wnt signaling and reporter activation, as evidenced by the induction of luciferase in a wnt reporter system.

Example 2

Figure 6:
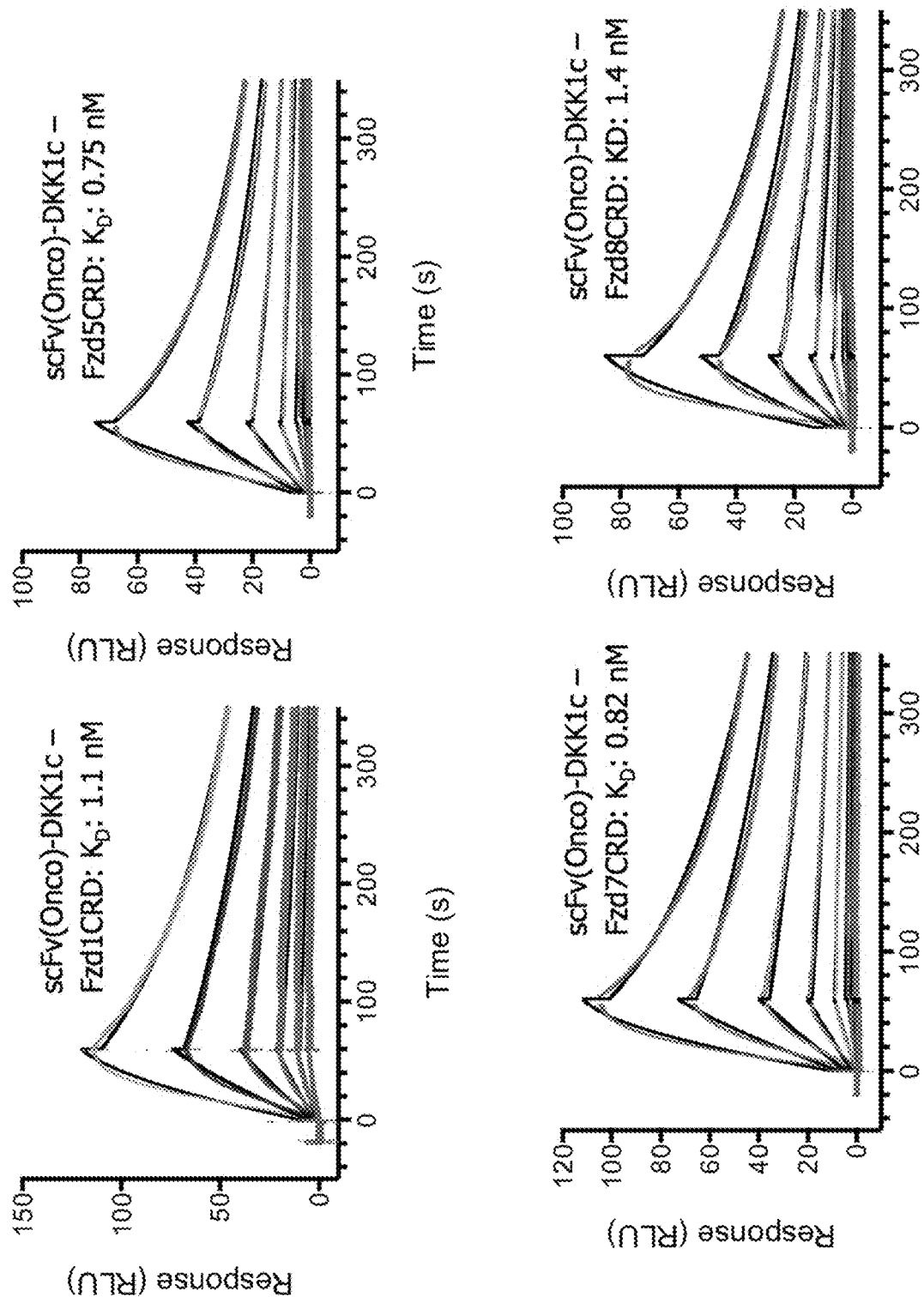
FIG. 6. Surface plasmon resonance experiments measuring binding of soluble scFv(Onco)-DKK1c to Fzd1CRD, Fzd5CRD, Fzd7CRD and Fzd8CRD immobilized on a Biacore chip.
Figures 7A, 7B:
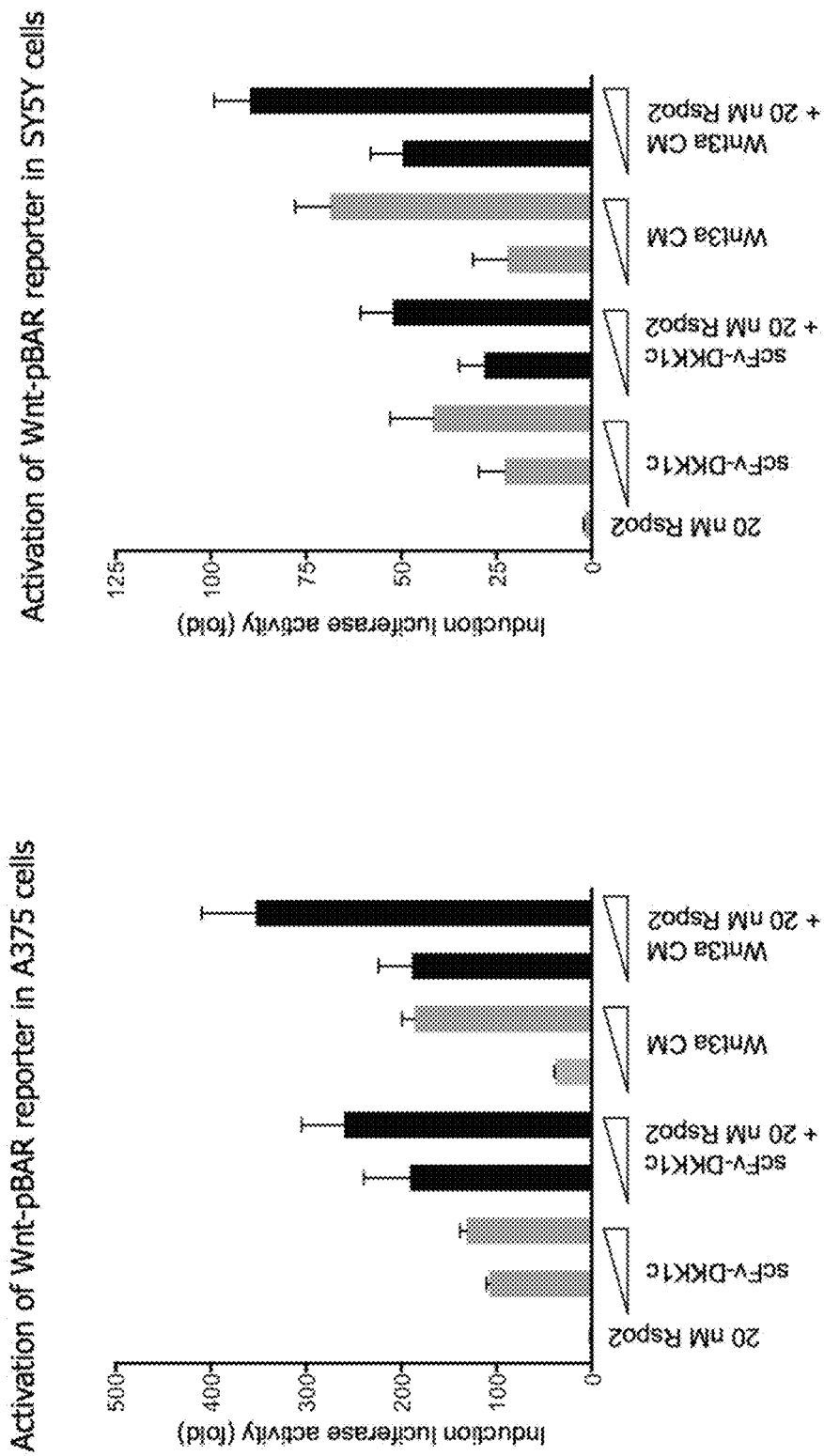
FIG. 7A-7B. R-Spondin 2 (Rspo2) enhances the activity of the Wnt surrogate agonist scFv(Onco)-DKK1c (DKK1c) to activate the expression of the Wnt-signaling dependent luciferase reporter in A375 pBAR cells (FIG. 7A) and SY5Y pBAR cells (FIG. 7B) in a comparable manner as it enhances the activity of Wnt3a delivered in conditioned medium. Assay was performed as in FIG. 4, with the exception that cells were stably transfected with the Wnt-dependent pBAR reporter, which contains concatamers of 12 TCF/LEF binding sites upstream of the firely luciferase reporter.

FIGS. 5-15 illustrate the structure and binding properties of antibody based wnt surrogate proteins, and the frizzled binding domains. FIG. 5 provides the amino acid sequence of an exemplary antibody based surrogate wnt agonist, depicting the scFv domain, and the wnt binding domain. The scFv(Onco)-DKK1c, comprises the scFv fragment of the OMP-18R5 antibody (Oncomed), and the C-terminal domain of DKK-1, fused by a flexible linker. The binding activity of the surrogate is shown in FIG. 6. Illustrated in FIG. 7, R-Spondin 2 enhances the activity of the Wnt surrogate scFv(Onco)-DKK1c to activate Wnt signaling in a Wnt-like manner, shown with the enhanced expression of the Wnt-dependent luciferase reporter in A375 amd SY5Y cells.

Figures 8A, 8B:
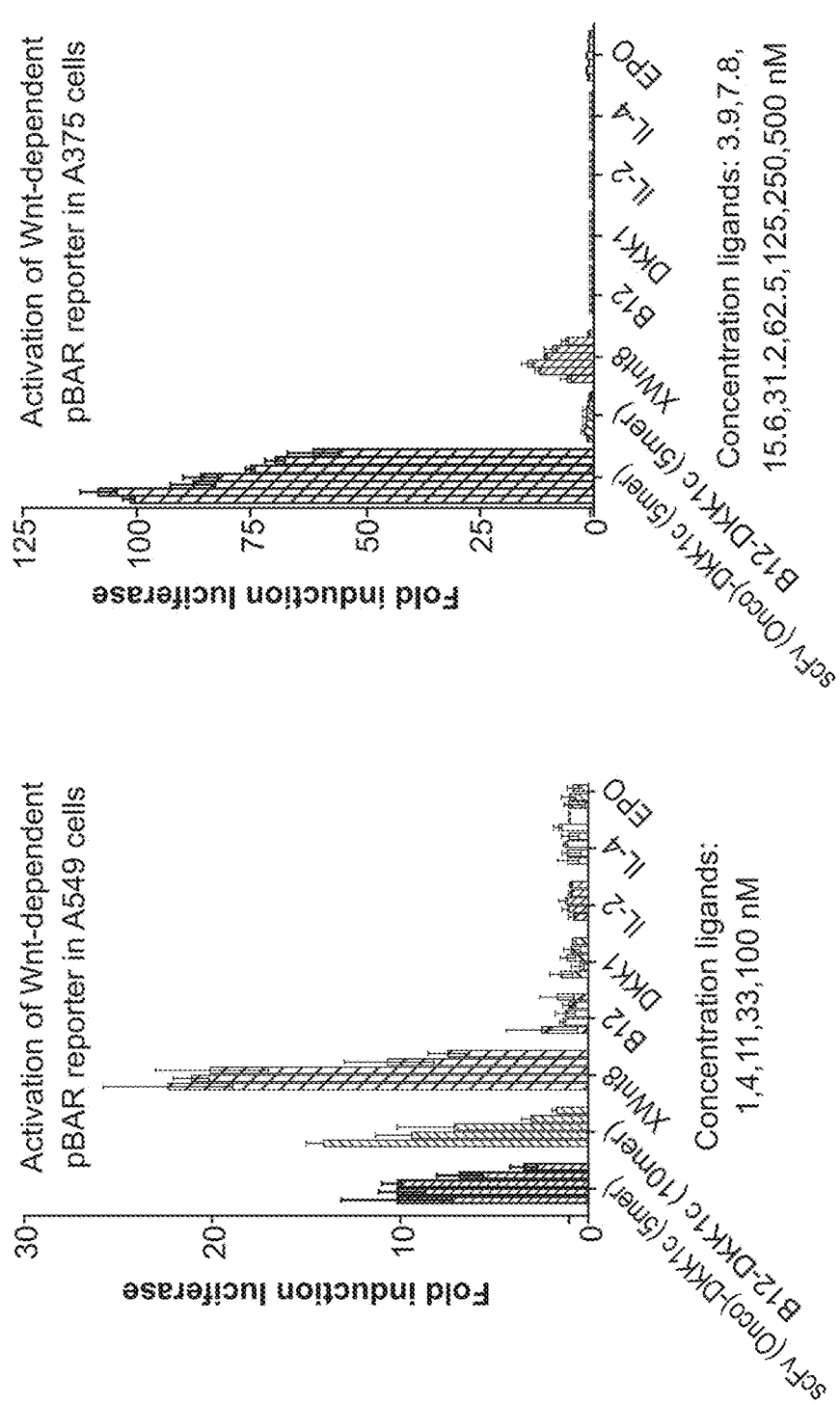
Figure 8C:
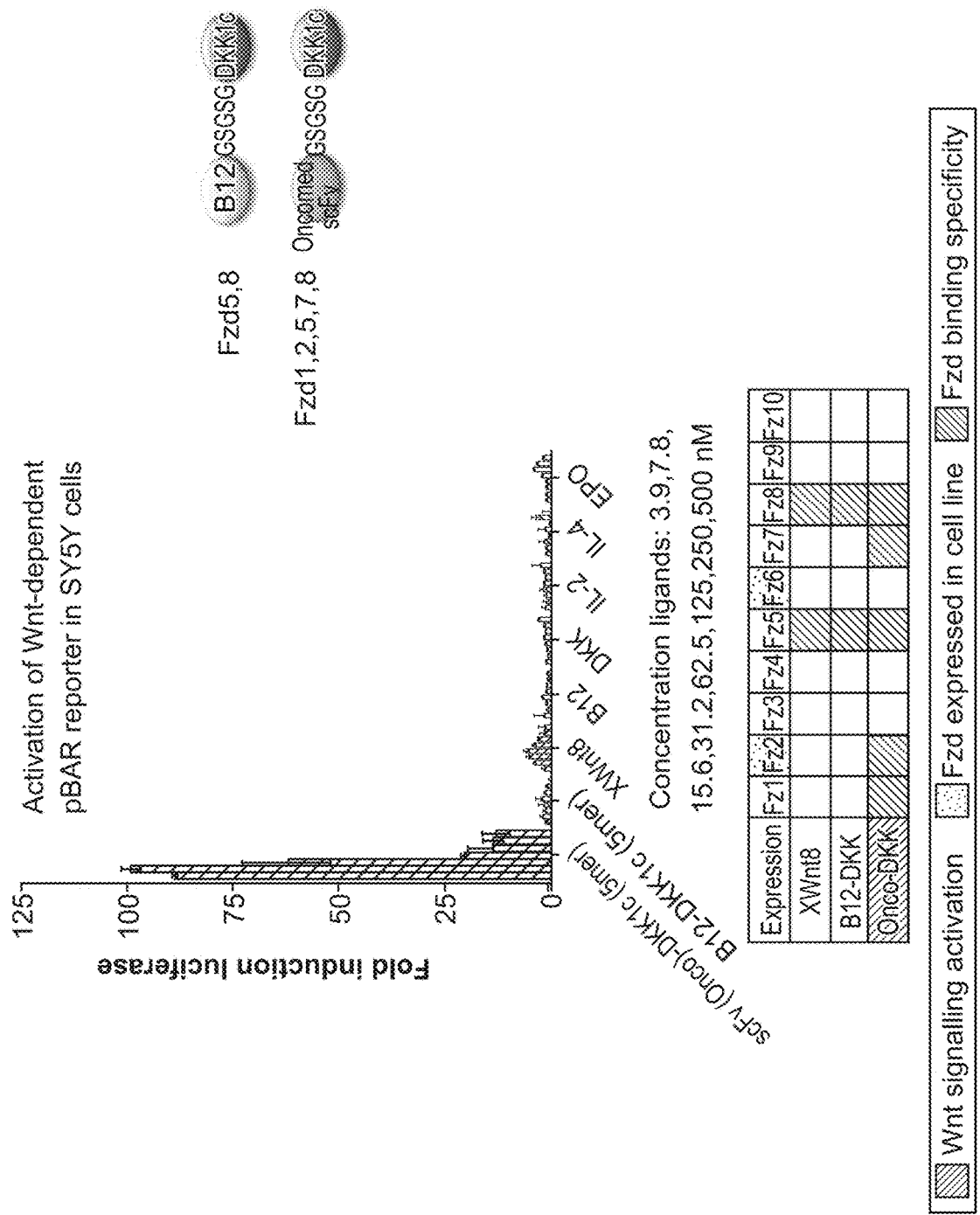
Figure 9C:
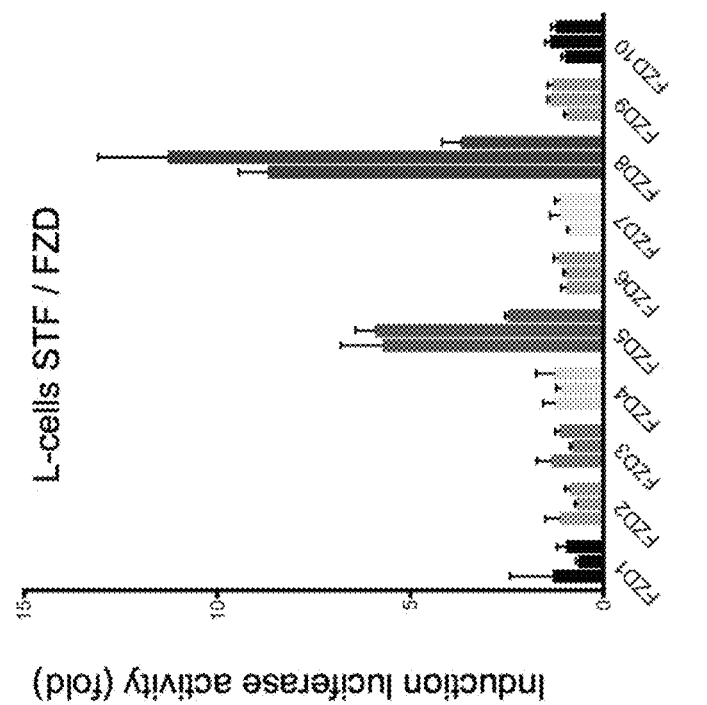
FIG. 9A-9C. Frizzled-subtype specific activation of the Wnt-signaling-dependent SuperTopFlash reporter by the surrogate ligands in L-cells.
Figure 9B:
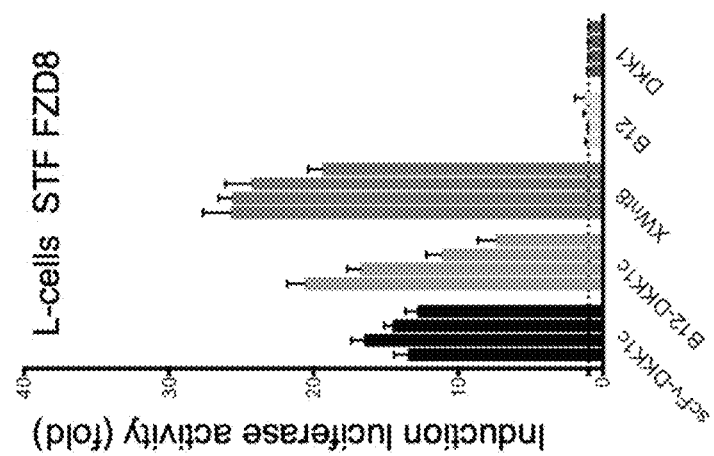
Figure 9A:
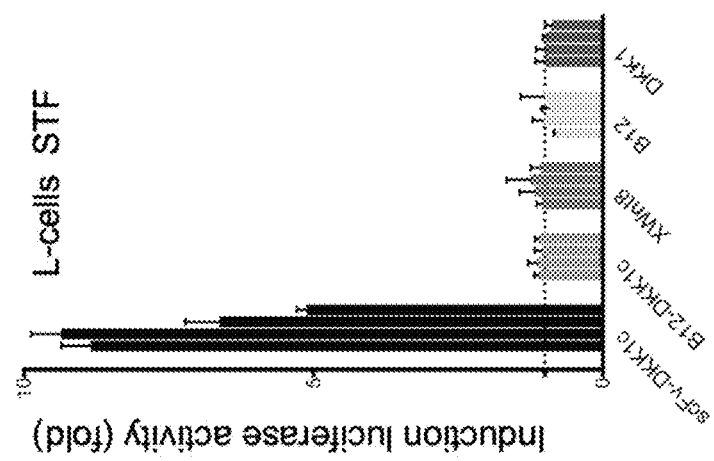

Activation of the Wnt-dependent pBAR reporter (firefly luciferase under the control of TCF/LEF transcription factor binding sites) stably transfected into the A) non-small cell lung cancer cell line A549 B) melanoma cell line A375 and C) neural blastoma cell line SY5Y in the presence of wnt surrogates is shown in FIG. 8 and FIG. 9. Activity of the scFv-DKK1c and B12-DKK1c (as described in Example 1) surrogate ligands, XWnt8, B12, DKK1, and unrelated proteins to induce the expression of the pBAR reporter was measured at various different concentration (indicated underneath the diagram). Fold induction of the pBAR reporter relative to basal activity is indicated. Frizzled reactivity of scFv-DKK1c, B12-DKK1c and XWnt8 is indicated, Frizzled expression profile of the corresponding cells was determined by qPCR and indicated, and Wnt reporter activation of corresponding ligands is indicated in the tables underneath the diagrams.

Figure 10:
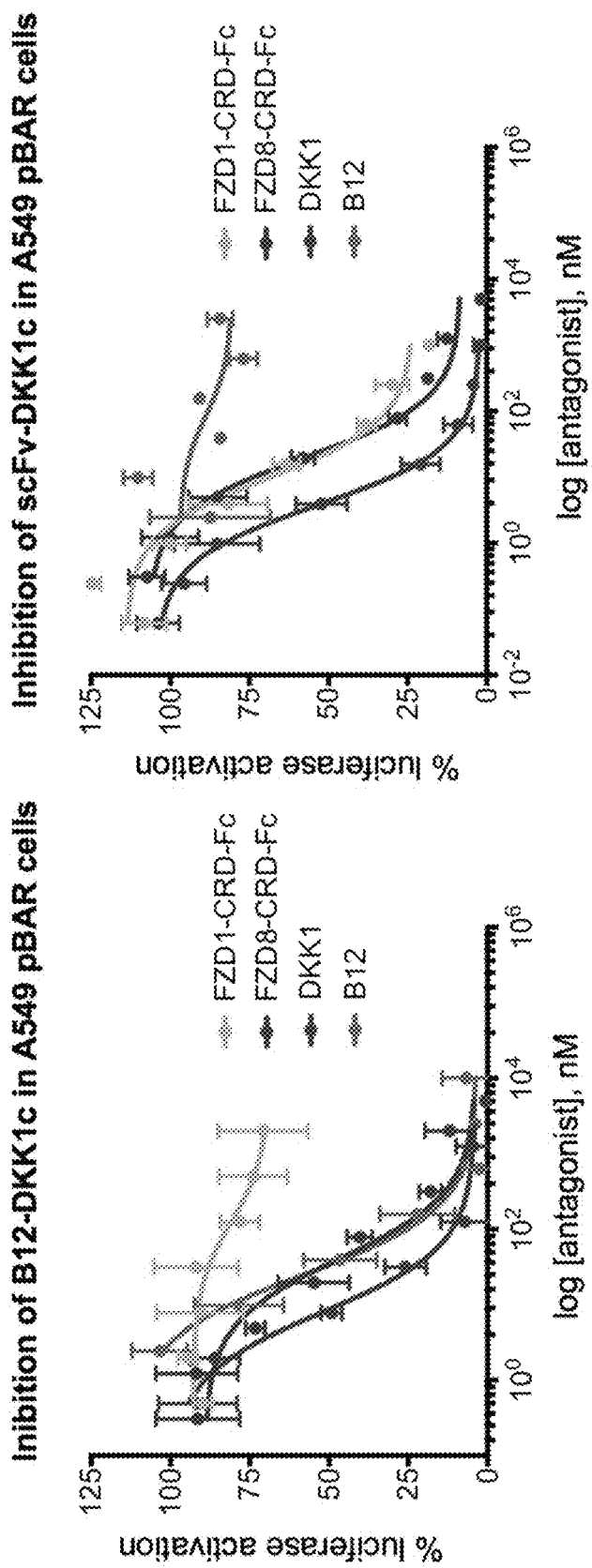
FIG. 10. The activity of B12-DKK1c to induce the expression of the Wnt-signaling dependent pBAR reporter in A549 cells can be inhibited by Fzd8CRD-Fc (via binding to B12), DKK-1 (via binding to Lrp5/6), and B12 (via binding to Fzd5 and Fzd8), but not by Fzd1CRD-Fc as it does not bind to B12. The activity of scFv(Oncomed)-DKK1c to induce the expression of the Wnt-signaling dependent pBAR reporter in A549 cells can be antagonized by Fzd1CRD-Fc, Fzd8CRD-Fc (via binding to scFv-DKK1c) and DKK-1 (via binding to Lrp5/6) but not by B12, as B12 does not inhibit binding of scFv(Onco) to Frizzleds. The assay was performed as in FIG. 4.

The activity of B12-DKK1c to induce the pBAR reporter in A549 cells can be inhibited by Fzd8CRD-Fc (via binding to B12), DKK-1 (via binding to Lrp5/6), and B12 (via binding to Fzd5 and Fzd8), but not by Fzd1CRD-Fc as it does not bind to B12, shown in FIG. 10. The activity of scFv(Oncomed)-DKK1c to induce the pBAR reporter in A549 cells can be antagonized by Fzd1CRD-Fc, Fzd8CRD-Fc (via binding to scFv-DKK1c) and DKK-1 (via binding to Lrp5/6) but not by B12, as B12 does not inhibit binding of scFv(Onco) to Frizzleds.

Figure 11:
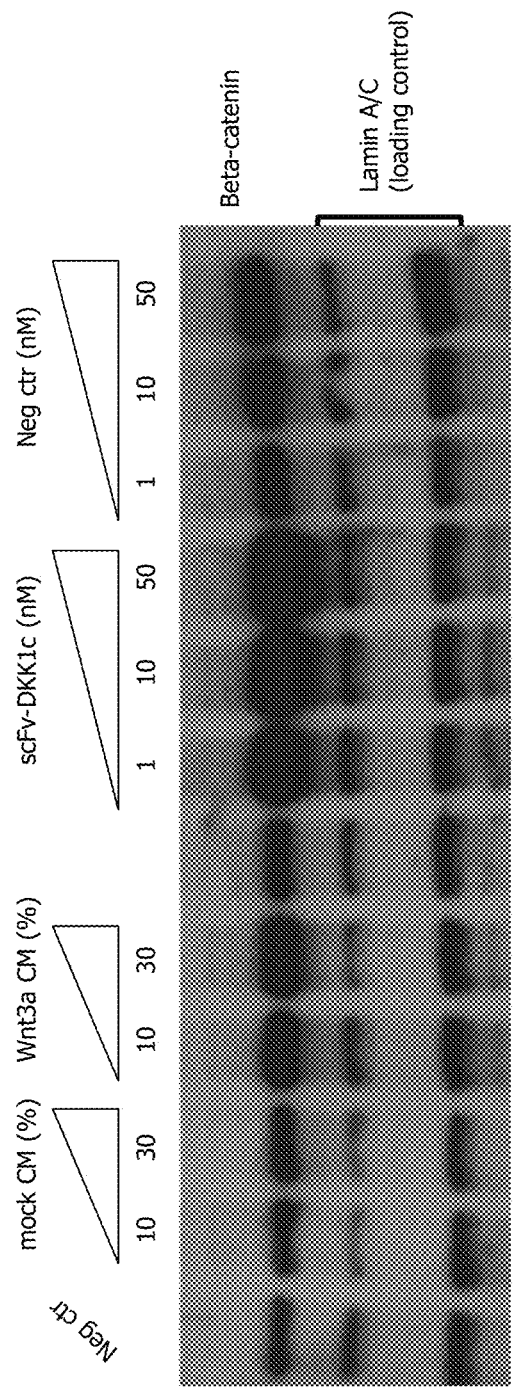
FIG. 11. Treatment of SY5Y pBAR cells with increasing concentration of scFv(Onco)-DKK1c, or Wnt3a containing conditioned medium (CM) for 2 hrs leads to the accumulation of cytoplasmic beta-catenin, compared to treatment with plain medium (neg ctr), neg control protein B12 (Neg ctrl (nM)), or control conditioned medium (mock CM). Cells were treated for 2 hrs with the indicated treatments, after which, cells were lysed in isotonic lysis buffer, and cytoplasmic beta-catenin was detected from the soluble fraction by western blotting. Lamin A/C was used as a loading control.

FIG. 11 shows the biological activity of the wnt surrogate. Treatment of SY5Y cells with increasing concentration of scFv(Onco)-DKK1c, or Wnt3a containing conditioned medium (CM) for 2 hrs leads to the accumulation of cytoplasmic beta-catenin, compared to treatment with plain medium (neg ctr), or control conditioned medium (mock CM).

Figure 12:
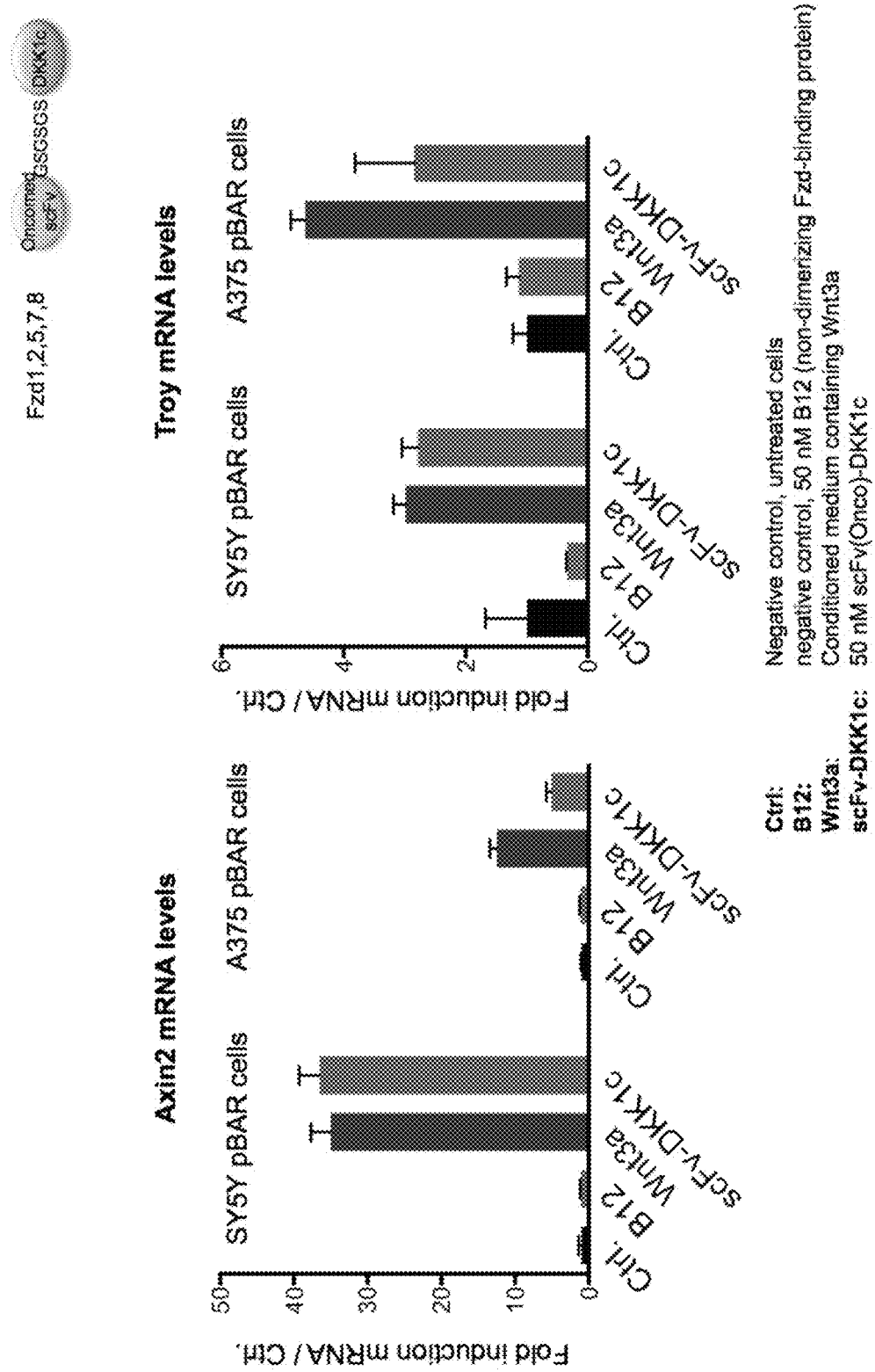
FIG. 12. scFv (Onco) DKK1c induces the transcription of the direct Wnt target genes Axin2 and Troy in various cell lines in a Wnt-like manner. SY5Y pBAR cells and A375 pBAR cells were treated with 50 nM scFv(Onco)-DKK1c, 50 nM B12 or 30% Wnt3a-L conditioned medium for 24 hrs. mRNA was extracted, reverse transcribed to cDNA, and qRT-PCR was used to detect levels of the Wnt target gene Axin2 and Troy transcripts. The sequence shown has SEQ ID NO: 19.

The scFv (Onco)-DKK1c induces the transcription of the direct Wnt target genes Axin2 and Troy in various cell lines in a Wnt-like manner, shown in FIG. 12. SY5Y pBAR cells and A375 pBAR cells were treated with 50 nM scFv(Onco)-DKK1c, 50 nM B12 or 30 Wnt3a-L conditioned medium for 24 hrs. mRNA was extracted, reverse transcribed to cDNA, and qRT-PCR was used to detect levels of the Wnt target gene Axin2 and Troy.

Varying the length of the flexible linker of the surrogate Wnts alters the signaling amplitude. FIG. 13A, A549 pBAR cells in the presence of 2 µM IWP-2 were treated with 50 nM XWnt8, B12-DKK1c with 0 aa, 5aa, 10aa and 15aa linkers, or 30% Wnt3a-L conditioned medium for 24 hrs. mRNA was extracted, reverse transcribed to cDNA, and qRT-PCR was used to detect levels of the Wnt target gene Axin2. FIG. 13B, A540 pBAR cells in the presence of 2 uM IWP-2 were treated with increasing concentration of XWnt8 and B12-DKK1c with variable linkers, for 16-20 hrs. After, cells were lysed, and the expression of the Wnt-dependent luciferase was detected with the Dual-Luciferase reporter assay system. It can be seen that signaling can be modulated, where a direct fusion is less active than the 5 mer and 15 mer linker, but the activity does down with increasing length, shown by the 15mer.

Figure 14:
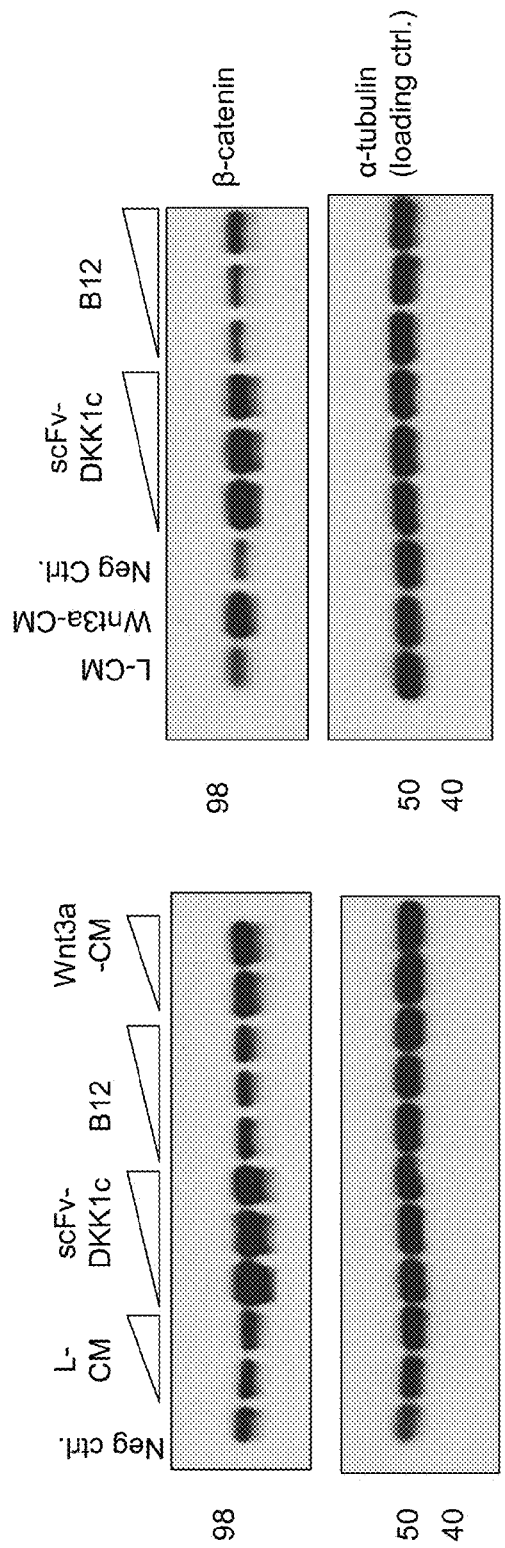
FIG. 14. scFv(Onco)-DKK1c enhances the accumulation of cytoplasmic beta-catenin in SY5Y and A375 cells in a Wnt-like manner. SY5Y and A375 cells were treated for 2 hrs with indicated concentration of scFv(Onco)-DKK1c, conditioned medium, or negative control. After 2 hrs, the cells were lysed in isotonic lysis buffer, and cytoplasmic beta-catenin was detected from the soluble fraction by western blotting. Alpha-tubulin was used as a loading control. The sequence shown has SEQ ID NO: 19.

FIG. 14. scFv(Onco)-DKK1c enhances the accumulation of cytoplasmic beta-catenin in SY5Y and A375 cells in a Wnt-like manner. SY5Y and A375 cells were treated for 2 hrs with drug, conditioned medium, or negative control. After 2 hrs, the cells were lysed in isotonic buffer, and cytoplasmic beta-catenin was detected from the soluble fraction by western blotting. Alpha-tubulin was used as a loading control.

R-spondin 2 potentiates activity of scFv(Onco)-DKK1c in a Wnt-like manner. 293 cells stably transfected with the SuperTopFlash Wnt reporter were treated for 16-20 hrs with scFv(Onco)-DKK1c (4 nM, 8 nM, 16 nM, 31 nM, 62 nM) Wnt3a (23% 29%, 33%, 38%, 41%, 44%) with and without 20 nM Rspo2 for 16-20 hrs, shown in FIG. 15.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. A water soluble canonical Wnt signaling agonist that dimerizes a Frizzled (Fzd) receptor with Lrp5/6,
    wherein the Wnt signaling agonist comprises a Fzd binding domain and a Lrp5/6 binding domain;
    wherein the Fzd binding domain comprises the amino acid sequence set forth in SEQ ID NO:17 or SEQ ID NO:18, and binds one or more Fzd proteins;
    wherein the Lrp5/6 binding domain comprises DKK-1 C-terminal domain; and wherein the Fzd binding domain and the Lrp5/6 binding domain are joined through a linker that enforces a distance between the Fzd binding domain and the Lrp5/6 binding domain of less than about 100 angstroms.

2. The Wnt signaling agonist of claim 1, wherein the linker comprises one or more glycine and serine residues.

3. The Wnt signaling agonist of claim 1, wherein the linker of from about 1 to 30 amino acids in length.

4. The Wnt signaling agonist of claim 1, wherein the DKK-1 c-terminal domain comprises the amino acid sequence set forth in SEQ ID NO:25.

5. A pharmaceutical composition comprising the Wnt signaling agonist of claim 1, and a pharmaceutically acceptable excipient.

* * * * *